US009662357B2

(12) United States Patent
Lebaron et al.

(10) Patent No.: US 9,662,357 B2
(45) Date of Patent: May 30, 2017

(54) BACTERIUM AND EXTRACTS OF SAID BACTERIUM AND THE USE OF SAME IN DERMATOLOGY

(71) Applicants: PIERRE FABRE DERMO-COSMETIQUE, Boulogne-Billancourt (FR); UNIVERSITE PIERRE ET MARIE CURIE (PARIS VI), Paris (FR); CENTRE NATIONAL DE LA RECHERCHE SCIENTIFIQUE (CNRS), Paris (FR)

(72) Inventors: Philippe Lebaron, banyuls-sur-mer (FR); Muriel Bourrain, Sorède (FR); Nathalie Castex-Rizzi, Colomiers (FR); Thien Nguyen, Rouffiac Tolosan (FR); Bertrand Chol, Villy le Pelioux (FR)

(73) Assignees: PIERRE FABRE DERMO-COSMETIQUE, Boulogne-Billancourt (FR); UNIVERSITE PIERRE ET MARIE CURIE (PARIS 6), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/626,589

(22) Filed: Feb. 19, 2015

(65) Prior Publication Data
US 2015/0231187 A1 Aug. 20, 2015

Related U.S. Application Data

(63) Continuation of application No. 13/997,029, filed as application No. PCT/EP2011/073747 on Dec. 22, 2011, now Pat. No. 9,084,811.

(30) Foreign Application Priority Data

Dec. 22, 2010 (FR) ...................................... 10 61081

(51) Int. Cl.
| | | |
|---|---|---|
| A01N 63/02 | (2006.01) | |
| A01K 35/00 | (2006.01) | |
| C12P 1/04 | (2006.01) | |
| C12N 1/12 | (2006.01) | |
| C12N 1/20 | (2006.01) | |
| A61K 35/74 | (2015.01) | |
| A61K 8/99 | (2017.01) | |
| A61Q 19/00 | (2006.01) | |
| A61Q 19/10 | (2006.01) | |

(52) U.S. Cl.
CPC ................ A61K 35/74 (2013.01); A61K 8/99 (2013.01); A61Q 19/007 (2013.01); A61Q 19/10 (2013.01); A61K 2800/40 (2013.01)

(58) Field of Classification Search
None
See application file for complete search history.

(56) References Cited

U.S. PATENT DOCUMENTS

| 2005/0074431 A1* | 4/2005 | Martin et al. ................ 424/93.4 |
|---|---|---|
| 2009/0022819 A1 | 1/2009 | Gueniche et al. |
| 2009/0028805 A1 | 1/2009 | Gueniche et al. |
| 2009/0028826 A1 | 1/2009 | Breton et al. |

FOREIGN PATENT DOCUMENTS

| EP | 2018891 A1 | 1/2009 |
|---|---|---|
| FR | 2658419 | 8/1991 |
| WO | WO 91/04742 | 4/1991 |
| WO | WO 2005/025614 A2 | 3/2005 |
| WO | WO 2005/030133 A2 | 4/2005 |
| WO | WO 2008/109669 A2 | 9/2008 |
| WO | WO 2009/130618 A2 | 10/2009 |
| WO | WO 2009/132244 A1 | 10/2009 |
| WO | WO 2010/050903 A1 | 5/2010 |
| WO | WO 2010/135704 A2 | 11/2010 |

OTHER PUBLICATIONS

Abraham et al., "Expression of Protease-activated Receptor-2 by Osteoblasts", Bone, vol. 26, No. 1, Jan. 7-14, 2000, pp. 7-14.
Abraham et al., "Inflammatory Bowel Disease", N Engl J Med, vol. 361, No. 21, Nov. 19, 2009, pp. 2066-2078.
Andersen-Nissen et al., "Evasion of Toll-like receptor 5 by flagellated bacteria", PNAS, vol. 102, No. 26, Jun. 28, 2005, pp. 9247-9252, XP002649208.
Arijs et al., "Mucosal Gene Expression of Antimicrobial Peptides in Inflammatory Bowel Disease Before and After First Infliximab Treatment", Plos One, vol. 4, Iss. 11, Nov. 2009, e7984, 10 pages provided.
Bieber et al., "Atopic Dermatitis", The New England Journal of Medicine, vol. 358, No. 14 (2008) pp. 1483-1494.
Cenac et al., "Induction of Intestinal Inflammation in Mouse by Activation of Proteinase-Activated Receptor-2", American Journal of Pathology, vol. 161, No. 5, Nov. 2002, pp. 1903-1915.
French Search Report issued in French Patent Application No. 1061081 on Dec. 22, 2010.

(Continued)

*Primary Examiner* — Chris R Tate
*Assistant Examiner* — Douglas F White
(74) *Attorney, Agent, or Firm* — Birch, Stewart, Kolasch & Birch, LLP

(57) ABSTRACT

The present invention relates to a novel bacterial strain isolated from groundwater. The invention also relates to bacterial extracts and to the use of same in the context of the treatment of inflammations. More particularly, the present invention relates to novel compositions of interest in the treatment and the prevention of inflammatory disorders, notably dermatological pathologies.

10 Claims, 8 Drawing Sheets

(56) References Cited

OTHER PUBLICATIONS

Glaser et al., "Antimicrobial psoriasin (S100A7) protects human skin from *Escherichia coli* infection", Nature Immunology, vol. 6, No. 1 (2005) pp. 57-64.
Gläser et al., "The Antimicrobial Protein Psoriasin (S100A7) Is Upregulated in Atopic Dermatitis and after Experimental Skin Barrier Disruption", Journal of Investigative Dermatology, vol. 129, 2009, pp. 641-649.
Gueniche et al., "Improvement of atopic dermatitis skin symptoms by Vitreoscilla filiformis bacterial extract", Eur. J. Dermatol, vol. 16, No. 4 (2006) pp. 380-384.
Hayashi et al., "The innate immune response to bacterial flagellin is mediated by Toll-like receptor 5", Nature, vol. 410, Apr. 26, 2001, pp. 1099-1103, XP002971120.
Hill et al., "Intestinal Bacteria and the Regulation of Immune Cell Homeostasis", Annu. Rev. Immunol., vol. 28, 2010, pp. 623-670 (47 pages provided).
Holzhausen et al., "Protease-Activated Receptor-2 Activation a Major Role in the Pathogenesis of Porphyromonas gingivalis Infection", American Journal of Pathology, vol. 168, No. 4, Apr. 2006, pp. 1189-1199.
International Search Report and Written Opinion of the International Searching Authority for International Application No. PCT/EP2011/073749 dated Mar. 26, 2012 (Forms PCT/ISA/220, PCT/ISA/210, and PCT/ISA/237).
International Search Report issued in International Application No. PCT/EP2011/073747 on Mar. 30, 2012.
Kaser et al., "Inflammatory Bowel Disease", Annu. Rev. Immunol., vol. 28, 2010, pp. 573-621.
Lau et al., "*Aquitalea magnusonii* gen. nov., sp. nov., a novel Gram-negative bacterium isolated from a humic lake", International Journal of Systematic and Evolutionary Microbiology, vol. 56 (2006) pp. 867-871.
Lourbakos et al., "Arginine-Specific Protease from Porphyromonas gingivalis Activates Protease-Activated Receptors on Human Oral Epithelial Cells and Induces Interleukin-6 Secretion", Infection and Immunity, vol. 69, No. 8, Aug. 2001, pp. 5121-5130.

Needleman et al, "A General Method Applicable to the Search for Similarities in the Amino Acid Sequence of Two Proteins", J. Mol. Biol., vol. 48 (1970) pp. 443-453.
Padovan et al., "How pattern recognition receptor triggering influences T cell responses: a new look into the system", Science Direct Trends in Immunology, vol. 28, No. 7 (2007) pp. 308-314.
Pearson et al., "Improved tools for biological sequence comparison", Proc. Natl. Acad. Sci. USA., vol. 85 (1988) pp. 2444-2448).
Rogers et al., "Microbial Cell Walls and Membranes", Chapman & Hall, London (1980) p. 564, ISBN 0-412-12030-5.
Sambrook et al., "Molecular Cloning a Laboratory Manual", 3rd Edition, vol. 3, Cold Spring Harbor Laboratory Press, Cold Spring Harbor, NY (2001).
Sambrook et al., "Molecular Cloning: A Laboratory Manual", Cold Spring Harbor Laboratory Press, Third Edition, vol. 3, 2001, pp. 15.40-15.43.
Smith et al., "Comparison of Biosequences", Advances in Applied Mathematics, vol. 2 (1981) pp. 482-489.
Smith et al., "Toll-like receptor 5 recognizes a conserved site on flagellin required for protofilament formation and bacterial motility", Nature Immunology, vol. 4, No. 12, Dec. 2003, pp. 1247-1253, XP002999619.
Steinhoff et al., "Proteinase-Activated Receptor-2 Mediates Itch: A Novel Pathway for Pruritus in Human Skin", The Journal of Neuroscience, vol. 23, No. 15 (2003) pp. 6176-6180.
Tatusova et al., "BLAST 2 Sequences, a new tool for comparing protein and nucleotide sequences", FEMS Microbiology Letters, vol. 174 (1999) pp. 247-250.
Vergnolle, "Protease-activated receptors as drug targets in inflammation and pain", Pharmacology & Therapeutics, vol. 123 (2009) pp. 292-309.
Vergnolle, "Clinical Relevance of Proteinase Activated Receptors (PARS) in the Gut", Gut, vol. 54, 2005, pp. 867-874.
Williams et al. "How epidemiology has challenged 3 prevailing concepts about atopic dermatitis", Journal of Allergy and Clinical Immunology, vol. 118, No. 1 (2006) pp. 209-213.
Wilsmann-Theis et al., "Facing psoriasis and atopic dermatitis: are there more similarities or more differences?", Eur. J. Dermatol, vol. 18, No. 2 (2008) pp. 172-180.
U.S. Appl. No. 13/997,022, filed Jun. 21, 2013.

\* cited by examiner

SEQUENCE LISTING

<160> NUMBER OF SEQ ID NOS: 2

<210> SEQ ID NO 1
<211> LENGTH: 1487
<212> TYPE: DNA
<213> ORGANISM: artificial
<220> FEATURE:
<223> OTHER INFORMATION: Novel bacteria LMB64, belonging to the class of betaproteobacteria, from groundwater

<400> SEQUENCE: 1

```
agtttgatca tggctcagat tgaacgcggg cggcatgctt tacacatgca agtcgaacgg      60
cagcacgggc ttcggcctgg tggcgagtgg cgaacgggtg agtaatgcgt cggaacgcgc     120
cgagtagtgg gggataacgc agcgaaagct gtgctaatac cgcatacgta ctgaggtaga    180
aagtggggga ccttcgggcc tcacgctatt cgagcggccg acgtctgatt agctagttgg    240
tggggtaaag gcccaccaag gcgacgatca gtagcgggtc tgagaggatg atccgccaca    300
ctgggactga gacacggccc agactcctac gggaggcagc agtggggaat tttggacaat    360
gggcgcaagc ctgatccagc catgccgcgt gtctgaagaa ggccttcggg ttgtaaagga    420
cttttgtccg ggagcaaagc ctgcttgtta ataccgagtg gggatgagag taccggaaga    480
ataagcaccg gctaactacg tgccagcagc cgcggtaata cgtagggtgc aagcgttaat    540
cggaattact gggcgtaaag cgtgcgcagg cggttgtgca agtctgatgt gaaagccccg    600
ggctcaacct gggaacggca ttggagactg cacggctaga gtgcgtcaga gggggtaga    660 attccacgtg tagcagtgaa atgcgtagag atgtggagga ataccgatgg cgaaggcagc    720
cccctgggat gacactgacg ctcatgcacg aaagcgtggg gagcaaacag gattagatac    780
cctggtagtc cacgccctaa acgatgtcaa ttagctgttg ggggtttgaa tccttggtag    840
cgaagctaac gcgtgaaatt gaccgcctgg ggagtacggc cgcaaggtta aaactcaaag    900
gaattgacgg ggacccgcac aagcggtgga tgatgtggat taattcgatg caacgcgaaa    960
aaccttacct gctcttgaca tgtaccgaag cctgaagaga tttgggtgtg cccgaaaggg   1020
agcggtaaca caggtgctgc atggctgtcg tcagctcgtg tcgtgagatg ttgggttaag   1080
tcccgcaacg agcgcaaccc ttgtcattag ttgccatcat ttggttgggc actctaatga   1140
gactgccggt gacaaaccgg aggaaggtgg ggatgacgtc aagtcctcat ggcccttatg   1200
agcagggctt cacacgtcat acaatggtcg gtacagaggg tcgccaagcc gcgaggtgga   1260
gccaatctca gaaagccgat cgtagtccgg atcgcactct gcaactcgag tcgtgaagt    1320 cggaatcgct agtaatcgca gatcagcatg ctgcggtgaa tacgttcccg ggtcttgtac   1380
acaccgcccg tcacaccatg ggagtggggg ataccagaag tgggtaggct aaccgcaagg   1440
gaggccgctt accacggtat gcttcatgac tggggtgaag tcgtaac                 1487
```

<210> SEQ ID NO 2
<211> LENGTH: 10948
<212> TYPE: DNA
<213> ORGANISM: artificial
<220> FEATURE:
<223> OTHER INFORMATION: Novel bacteria LMB64, belonging to the class of betaproteobacteria, from groundwater

<400> SEQUENCE: 2

```
gggcgcagca ccatcgccca ggccaaaagc cacccgtgcc gattcggcgg cctgttgctc      60
gcgctcaatg cgctgcgcct ggtcggccaa gtcggcggct tgctgctcgg ccttgcccgc    120
cagggtgtca cgctcgcggg tcagttccgc cacctgctcg gctagggcat cgcgctcggc    180
```

```
ctcgatcacc tcaccagcgg ccgccagctc ggcggcttcg ctctgcgcct ggaccaagcg    240
gccctcgacc tcggcgcggg cctgggcggc tgcgcgctcg atctcggcgg caatggcggc    300
ggtcaatgcc tggggcagtt ccggcgcagc agcagcggcc accggccggg cctctcgcca    360
ggcagttaga tgcttgtgaa cggtattcgg gctgccggtg cccaaacgct cgcggatcgc    420
gcggatagtc ggctgctgcc cttcgccgac cagcgcatca gcggcggcgg cgaacgggtg    480
gcccgtgcag aggcccgcgt cgagcagatc gagcagcagg ccgccaaggc ggcacaggcc    540
cacgaagaag cccgcgccgc cgccacgcag gaagcccggc aagtgcaagc cgaacgcgac    600
gaagcccgca aggtggccgc cgaggcgcgc gagcagaccg cgcgcctggc tgggcaactc    660
gaagccctca ccgcgaagga gcgaaaagcc gatgaaagac cgtgaccaca acgaagcgat    720
ggccggcatg tttcaggccg accccccgatt tgccgccgac tatctgcgcc aggtgttggc    780
cgatggcgag cctaccgacg tgcgcgccgg cttgcggcaa atggcggatg tgctgcgcgt    840
cagtcaggcc gccgcgccga ccgattctgc gccttcggcg ggcctctttg accgggccgg    900
cgtgcgctac gaagtggcgt gcgatgtgat cggggcgttg attgcccatt acgccgaaat    960
catgggacgg gaacgcgagc aggcgcagcc gaatgaggcg gttttgcgcg tggcggagc    1020
catgaaggcg gcgctggccg gggagcggga tgatctcgat ccgcgcgata cgccggcat    1080
cgaggcggca atttcgcgct atgcgccact ggcgcgccgg ctgtatggcc aggctgaaaa    1140
cgaccacgcc cgccaggaac agcgtcgcgc cgatttcgac caggtgcatg cttcgctggc    1200
cttggagggc ctggccatga gcgcggacga tttggcggtt caggcgctgc tgatccgggg    1260
cgacattacc cacgatgagg cggtgcagtg ctaccgcatc ctgcatcgcc atgcgcggta    1320
aaaccgactg gccgcccgag gtggccggtg tgctgggttt gctcgaatcg cagccgccag    1380
aggcggcgat gctggtgggc tgttttctgg cggcggtagc ccatcccgat catgcggccg    1440
aattggcgat gttcgacaaa ttgccgccag cggcccggat ggtcgtcggg cgatttttcc    1500
tcgttttttct ggcgggcggc ctggacgatg ccgggcgcga aaaactgcat cgcacatgc    1560
aggcatggtt tgtccgtcag cgccgttttc ggtgaatggc ttgcctcatc cactagggcc    1620
gggcaagggg tgaacagcgg gcgatgctgg cttgcggac gaccccgcac ccccggaaaa    1680
cttgtcacac accacgcaac tcccgttgct tcgctaaaag ccttgtgccg caaggctttt    1740
agcgaggcga caccgaagac acatcgcggc gacaccgaaa gggccgaacc ggcctaaaac    1800
ccttgctgcg caaggagaac agccgcgctt tcgcgcgcga aagtgcttca aatgcctgtc    1860
ggcatcagca gggtatggat cggcacgccg aaggcgttgg cgatgcgctc caggttgtcc    1920
aaggagatgt ttctgacttg gcgctcgcag tgcgcaacga aggtgcgatg taggccgcac    1980
tcaaaggcga gcgcttcttg tgaccagcct ctttcccggc gtaatcggat catgttggcc    2040
gcgagcacgg cccgcgcgga atgcgcggtt ggtgcgggag gttgagcggc gggagacatg    2100
caaaccagtc tcctgatatg ccgcttttac gtcagccgtg tttaagtcac aatatggttt    2160
tctcatagag aaagacggcg tgacgatggg cagaaaaaca gcaatcaggc gaggggggtgc    2220
cgtgttggcc agcctgttga tttgcgcaat tgaaccggtc ggcgcggcct ccctggtcgg    2280
cggtcaaacc gatgattccg tgtgcgacct gggcagcgcg ccacagaacg cccggaagct    2340
gtcggcagcg ggcgacttca tccgcgcgca gtgcaaaaac ggtcaaatgt tggtgggttc    2400
cggcatcgtg cctgccggcg ggtttgactc ggaagtggtg cgcctggcgc gcaccttctg    2460
ccgcatggcg gacattcaga ctcggcgcac gcagggcaac atggccggcc tcgtcatgga    2520
```

```
gatcgacgag gtacggtgca tcatcgggaa gttgccgaca tgagaaaagc gatgttggct    2580
ggctttctgg ccgttgtggt ggccaacgtg gttgccgctg agggcggtgc gcccttgcgc    2640
ggcggtgttt gcatcggacc gttccgtggc gctgattccg tcgtgcactg cgagcacatc    2700
ggcaaggtga cgatccgcca gatttacgaa aagggctttc gggtcgttca catgcaggac    2760
gacaagaaca cagccagcta cgttgtgctg gttatcgagg agcaggcgcg atgagggcga    2820
aagcgtggcg gatgctgttt gccgggcggc gctgggtgct ctggcttccc gtgccggcgt    2880
cggtatggct ggcactgccc gaatggcagc acattcccgc catgttgttg gcggcctga    2940 tcgtgtggat tcccttctgg ctcgcgtggt ggctcagtga tggcttcgcg ggcatgtcca    3000
ggtggccagg aaccggcgca cctgcggtat ctggcggggt gaacccgcac accggcaagc    3060
catgcacggt gtatcaccag ccgtgggag ataccttcgt gggtggagac tgattatttg    3120
attgaggaac gatgacaagg gccagcaaca agctggccct tgtcgttttc tggactgttt    3180
tacccacaac atccgctctg ctgctgaatt ggcggacatg gcaccgagcc gaacgaacag    3240
aacacgcagc aatcccccgg cttggggcgc agcagcgtat ggcaggccgg gcactcgtag    3300
tagaactggc aggcgtccgt gggcatggtt tcctgctgtg cgtggccgca gtgcgggcag    3360
gtcagcacgg attcgagaat gacggcgctc atcgtggcgt tacctctgca cggtggacgg    3420
atagcctgcg ttcgtcgttg ccgaggtcaa cgcttccggc ttggccttgt cggcgtcata    3480
ggtgacggtg gccgttttct tgtcgaaatc gaccttgacg cgctcacac cgggcacttt    3540 ctccagcgac ttcttgactg tgatcgggca tagctcgcag gtcatgttct gaacggccag    3600
cgtgacggtt ttcggggtgg cggccagcac ggcgagcggc acggcagcca gcagagcaat    3660
cagcagtttg cgcatgggag tctcctttca atagaacagc ggggcgaacc acggcacggc    3720
caacagggca agcaacagca cagtgacgat ccagaacgtc aggcgctgcc gctggcgtgt    3780
gcgcggatca gcgcatggcg tgccgggcgt gcagacctgc ggcaccagat agagcttgcg    3840
gaaggccagt ccgagaaaga gcagcgtcat gccgatgaaa aagggccggt acggctccat    3900
cgcggtcagg ctgccaaccc atgagccacc aatgccaagc accagcagga caagcggccc    3960
gacacagcac accgacgcgc cgatggcggt cagtacgctc acgatcaacg agcttttttc    4020
agtgagtcgt gccatgtcgc tttccttgta cctgtttgcc caagtgttac tctaaatccc    4080
gtacctaagt acgagtcaa ggggtgtga tgggaacaga actgaccatc ggcaagctgg    4140
ctgacgctgc cggggtgaat atcgagacga ttcgctacta ccagcggcgc ggcctgctgg    4200
atgagccgcc taaccgcca ggggggcatc ggcgctatgc gcctgagcag gcaaaacgtg    4260
tgcgatttat caagcgggca caggcgcttg gtttcacgct ggacgaggta ggcgcgctac    4320
tgaccctgga tgcggcctgc gcctgcggtg agacgcgagc gctggctgtg cgcaagctgg    4380
gtctgatcga gcagaagatg gctgacctcg cggccatgcg gcaggcgctg ggtggattgg    4440
tgcagcagtg tgatgcgggc gacggtggag ccagctgtcc catcatcgac gtgctggcag    4500
gtaattagat gtgttcaaaa aatggtggtt ttctggacac atgccggttt gccctgtcct    4560
gagttgtcct gatgcgttaa agtgttcatt tattcgttca gctttcaatg tggcggaact    4620
gttcatgaat caacgcatcg gctatgcccg cgtttcgacc gacgaccaaa acctagacct    4680
gcaacgggac gcactccggc aggctggatg ctcaaccatt tacgaggaag cagccagcgg    4740
aaagagcgca gcaaggcccg agcttgagca gtgtcggaag gctctccggc ccggcgacac    4800
gcttgtggtg tggcggcttg atcgccttgg gcgcagcctg cccgacctgg tgcagatcgt    4860
ggctgatctt gaacagcgcg gcgtgcattt cgagagcctg accgagaaga tcgagacggg    4920
```

```
gagcgcagcg ggtaagctgc aattccatgt tttcgctgca ctcgccgagt tcgagcgcgg    4980
cctgatccgg gagcgaaccc gggcagggct ggatgcagct cgcgcccgtg gccgatccgg    5040
tggacgcaaa ccgaagctgg acgccaagca gatacgccac attaaggcgc tactacgtga    5100
cccgaatacc tgtgttgctg aactcgcccg tgactacggc gtgtcgagaa caactatcta    5160
taaacactgc ggtgtggttc tgccgcgtac agccgatgaa ggggcaatat gacaaaaaag    5220
acaacagcat tcgatgtatt cgagaaatgc gtccaagcag ttcaggctgg tgaactgatc    5280
gaatccgttt ctgcgaagga caaggaattc catttccaga actggtttca gaagcgcctc    5340
cagagcctgt cgatgcactt cgaggggtcg gtcgcaaca cctacccgga cttctgcttg     5400
gtagagcaca ccgagggcta cgagatcaag ggtttggcat ggcctggccg cgagcgcgac    5460
tacgactcga acagccaagt gccgactggc tatcacaacg gccgtcaaat cttctacgtg    5520
ttcgggcgct accccgcaga cctgtctggc tatgccgatc agggcaacgg ccgcaggcag    5580
tacccggtgg ttgacctcgt ggtctgccac ggcgacttcc tcaacgccga tcacaactac    5640
gtccataaga acaagagcgt aaagggcttt ggcacctacg gcgacatcat gatccgcgac    5700
cggaagatgt acgtcgcgcc gacgccattt gcgctgaccg aaggcaccac tggcctgatg    5760
actttgatcc tgccggagaa cttcggcacc gatgaccgtt accaggtggt cggtaacctc    5820
actcgcgtcg aggcggaaac gctggtggtt ggctacaact ttgacctgcg cacgaacgag    5880
ctgagcgcag agcgcgtgcc caatcccaac gcaggcaccc agcaccgatt cgtggcctac    5940
cggctcaagg atcaagcgag caagcctgtc tccatgactg caccaggt gcagcccgac     6000
gagaacaacc tgccggacga cgaatgaaca ccatcaccga caagatcggg ttcgcttacc    6060
cggttgcagc gaccgcgctg gagtgcgact tcccgctggt cgaaatcagc cagatcgccg    6120
agcaggaaag ttggcgaaag gagatcaaca ggccgatcta ccacatccac aagtggtggg    6180
cgaccagact tgggtcggtg tttcgtggca ttacccttgg tgctttgagt cagcctggta    6240
ctgacctctg ggcgcagttc tacaaaacgc acgacctggc cggtaaggta gtgctcgatc    6300
ccttcatggg cagtggcacg acgcttggcg aggccgtcaa gctgggtgcc aaggccatcg    6360
gctgcgacat caacccagtc agtaccttcc tcgtacgtca ggcgttcacg ccggcgtccg    6420
aggcagagct gcgtgccgct ttcgagcggc tggaacgtga cgtggcaccg gagattcggc    6480
gctactacca gacgcgcgat cctaagacgg gcgagctgat tcaggtcttg tactacttct    6540
gggtcaagac ggtgacgacg cccgagggcg aggtaatccc cttgctgtcg cgctacgtgt    6600
tttcacaaga cgcctacccg aagaagaagc gcgagcgca gatcgtgtgc cctggctgct    6660
ggagtgtgct ggaggatcgc tacgatgcga ctgacctgca ctgccagcac tgcggccacc    6720
agttcaatcc gcaggaaggc ccggccgctg gtcagtacgt caaaaccaag gccggtcacc    6780
gttaccgcat caaggaacta ctgccaaagg acggtacgcc gccctctcat cgaatgtacg    6840
cgatgatggc cttgcgagcg gatggatcga aggtctatct gccggtgcgg aatgaggact    6900
tggccctcta cgaggaagcc caagaacgcc ttgctacaga ggcactgccg ctgccgaaaa    6960
cctctgttcg acctggccac aacaccgacc aggcgcgcgg ctacaactac acccaatggc    7020
gcgacttctt caatgcgcgc caactgctgt gccttggcct gctgctgcgg gaaatcctga    7080
ccatcgacga cctggcagtg caagagcaga tgctgtgctt gttctccagc accttggagt    7140
tcaacaacct gttttgcagc ttcaagggtg agggaacagg ggccgtgcgg catatgttct    7200
cgaaccacat cctcaagcca gagcgcaccc cgctggagaa ctccgtgtgg ggcactggca    7260
```

```
agagcagcgg tacgtttagc acgttgttcg agtctcgcct gctacgtgcg aagcgctacc    7320
tcgatgagcc gttcgagatc gcgttcgagc atgaccagga cggtaaccgc gcaggctcgc    7380
gcaagacggt ggctagccat ccgatccgcg cccgtcgcgt cgaaacctgg ccggaattgg    7440
aggccgcaga tcatggcctg ctgatcctca acggtgacag ctcgaagctg ccggtgcccg    7500
ctggttcggt ggatgccgtg gtgactgatc cgccctactt cgacttcgtt cattactcgg    7560
agttgagcga cttcttttt gcttggctca ccctgtgct cgccagcgc tatccgtgga    7620 tggcccgcga ggactcgtct gaccaagggg aggtgcagca caaagaccct cgtgtgttcg    7680
cccgtcagct tgcgtcggtg ttcacggagg cgtgccgcgt gcttaaggac gatgagtgt    7740 tggcgttcag cttccaccac tcgcgtgccg agggctgggg ggccatctat gaagcgatca    7800
acaaggcggg cctggccgta gttgcggctc accctgtcca tgccgagctg cgcgcggcaa    7860
gtcccaagac tgcggccaaa gacccgatca gccttgatgc gattctggtg tgtcgcaaaa    7920
aggcgtttgc cctgcaccag tcgcctgcta tccaggatgt ccgccaggct gttgatgcgc    7980
tggcatcacg gctgcaagct gctggccttc gcatctcggc gggtgaccgc ttcgtgatcg    8040
gcgcagcgca aaccttgatt gcacgcgctg ctgatgacat gggcttcgac gagatcaagg    8100
ttgatcttga ggcaattcgg ctggccgtgg ggccaagggc tgcaacatca aaggctgcga    8160
gtgcgtggga tgacgatgtg cccttctgat tggctgcacg gccttgtcgg cgcatgcgtt    8220
ttgatggcag ccgctgcacg caagccgcgt ccctccgcgt aaagttcatt tatacgcaaa    8280
tacgtatttg cgtgatacaa taacgccata ttaatggagg tgcgtaaatg cggactattg    8340
ttgtggctag ccaaaaaggt ggcgtcggca agacaacgat tgcaggtcac ttgggtgtca    8400
tggccgagca gagcaaagag gggccagtgg cgctgatcga cacagaccca caaggctcgc    8460
tcgcgtcctg gtgaatgag cgaaccaatg aggcaccgct gtttgcacgg gtggaaatcg    8520
gcaagctgac cgagcacctt caggcattgt ccaagggtgg catcaagctg ccatcatcg    8580 acaccccgcc ctctgttacg gaaatgattc agcaggtgct ccgcaccgcc gacttggtac    8640
tgatccccac caggccgagt ccgcatgact tgcgcgcggt cggatctacc gtcgaactgg    8700
tggagaacgc aggcaagcga atgatcttcg tcatcaatgg ggcggcacct cgcgcgcgga    8760
tcgcgggtga ggctgccgtg gcgctttcgc agcatggcac ggttgccccc gtgacgctgt    8820
accagcgcac cgacttcgcc agctcgatga tcgacgccg caccgtccag gaaatcgacc    8880
ccaaggggcg gtcggccgaa gaaatcgggc agttgtggaa atacgtatct acacaactgc    8940
gtaaaatttg atataatacg tacatgcgta ttaatggaga tacgtaaatg gctaaaactg    9000
catctttgac tgccggcctg gtggccaaga aaggggaggc gtcccctgct acggttgtcg    9060 cggcaccccca ggttcaacct atcgaagtga aggcatcggc gactggcggc ggccgggatt    9120
actacaaggc gttgaccgtc aagttggatc gtgaccgcta cgagagtctg aaaagcatgg    9180
gcgtgaagct ggacaagaag agccaggaaa tctttgtcga ggccctggat ttgtggatga    9240
agtcggccgc tggccagcaa cacgcctaag aggcccctat gcgttcagtg cgctctgccg    9300
tcgaactcgc caaggagttg gccgaaaaag ccaaggcccg ccgcctagcg gcggaaaaga    9360
acgagctggg acttgaaggc ccggcgcagg gcaacgccgg caccactccc agcccggtga    9420
aggttgcggc cgaagtggtg ggcgagcagc cggcacgacg caagggagcg ccgaaagggc    9480
cgcgtggcct gatgccggtg catcatccaa accgcgattt cttcttgtgc gatctgtttg    9540 actacgcccct aaaggatgac ggcgtgagca tggaggcccc catcttcacc ttggcaacca    9600
ggccggacac ctctgttggg cattgggaaa gcaaggatgg gacacgcgcc atcaccgtca    9660
```

```
cgccaagcgt gaaggggagg gccacgcagt ttgataagga tttacttatt tacgtagtta   9720
gccagatgac cgaggctatc aatcgcggtc ggcctgatgc gaacaatcga accgtgcgct   9780
ttcgcgtcta tgactacttg gtctcaacca acaagccgac tggcggcaag gagtaccagc   9840
gactggagga tgccctagac aggctgcggg gtacatcgat caagacgaac atcaagacgg   9900
gtggccagcg tgtgaaggaa ggcttcggca tcgtcgatag ctggacgatc atcgagaagg   9960
ccccgacga tgaccgcatg attgccgtcg aggtcacgct ctccaagtgg cttttcaatg  10020
cagtgcaggc ccacgaggtt ctgaccatca acccggacta tttccggctg cgtaagccaa  10080
ttgagcgccg tttgtacgag ctggccagga agcactgtgg cgaccaggcc ttttttgtga  10140
ttgggctgga actgttgcag gacaagtgcg gcagcaagtc ggcactgttc gagttccgcc  10200
gtgccttgcg cgagatcatc aaggccgaca ccttgccaga ctaccgcatg acgcttgatg  10260
acgagaaaga ccaggtgatt ttctacaccc gcgacacgaa gaagctagcg gcgtctaccg  10320
ctctggcccg gcgcttccag tgacgcccaa agtattgacg gtcaatactt cgttatttca  10380
cccatgcggt gttaccgctg cgtgttggac gttcccttga cctagcggcc gaggcagggc  10440
tttcgcgctt tgcattgagc caccaagtgc gtctcgctcc ttcgagcatc aagccctaac  10500
gcgtttcatg tcactttcgc gcacgaaagt cgaggcaaga ggcttgatcg tgtctatcgt  10560
tacatcaccc atgcctgtgg atggacacgt tacatcaccc atgttttctg tggatgggca  10620
cgttacatca cccatacctc acttcgttac atcgcccatg cagcgatttg tggaagcctt  10680
gagcagcaag gctttacgag cgttatccac agccgtaaca cgcgcgcgcg attttttaac  10740
tttataaatc tttaacgcgg ttgcggacaa agcccgcgcc gcctcttggg ggctacgccc  10800
ccgccggctc ctacgggccg caagcggccc tccgcccgcg cttcgcgctc cctcccggca  10860
tccccgaggg gtttcgcttc gctgcacccc tcgcgcttcg cgctcacccg catatcgagg  10920
ccccaaagg gggccggatg gtgcccc                                       10948
```

BACTERIUM AND EXTRACTS OF SAID BACTERIUM AND THE USE OF SAME IN DERMATOLOGY

CROSS-REFERENCE TO RELATED APPLICATIONS

This application is a Continuation of co-pending application Ser. No. 13/997,029 filed on Jun. 21, 2013, which is a National Phase of PCT International Application No. PCT/EP2011/073747 filed on Dec. 22, 2011, which claims priority under 35 U.S.C. 119(a) to Patent Application No. 1061081 filed in France on Dec. 22, 2010. All of the above applications are hereby expressly incorporated by reference into the present application.

The present invention relates to a novel bacterial strain isolated from groundwater. The invention also relates to bacterial extracts and to the use of same in the context of the treatment of inflammations.

More particularly, the present invention relates to novel compositions of interest in the treatment and the prevention of inflammatory disorders, notably dermatological pathologies.

Dermatological diseases such as atopic dermatitis, pruritus, eczema and psoriasis are increasingly frequent in young children. The prevalence of atopic dermatitis has doubled or tripled in developed countries over the past 30 years: 15% to 30% of children and 2% to 10% of adults are affected (Williams H. et al., JACI 2006; 118:209-13). Atopic dermatitis is the cutaneous manifestation of atopy; it is a chronic inflammatory dermatosis or eczema, occurring due to a genetically determined set of circumstances. It is now regarded as a major public health concern. Atopic dermatitis is often associated with other atopic disorders such as allergic rhinitis and asthma. This affection most often appears during early childhood and is characterized by repeated outbreaks over several years. It progresses with flare-ups interrupted by spontaneous remissions.

The quality of life for patients suffering from atopic dermatitis is profoundly disturbed. Accepted treatments include topical corticosteroids and immunomodulators, systemic agents whose frequent side effects limit long-term use, and emollients. Current therapies are reactive—treatment of outbreaks—but it is now believed that early intervention focused on the control of outbreaks and of cutaneous inflammation can be beneficial in terms of both control of the disease and the potential appearance of asthma and/or rhinitis (Bieber, T. 2008, Atopic dermatitis, The New England Journal of Medicine, vol. 358(14) 1483-1494), as atopic dermatitis is regarded as the initial phase of atopic progression. In most cases, treatments include a local component in order to best provide relief to patients.

Standard treatments for atopic dermatitis notably use topical corticosteroids or immunosuppressants, although such treatments are not free of adverse effects in children in particular.

Atopic dermatitis is complex and multifactorial. In the literature, some epidemiological studies have shown that the "hygiene" factor in urban environments promote the disease like allergy and autoimmunity. On the other hand, in rural settings where man is in constant contact with microorganisms and/or allergens, such exposure stimulates man's defensive immune system from birth.

In atopic dermatitis, the barrier function of the skin is weakened and impaired, which promotes the invasion and the colonization of pathogens (bacteria, viruses), in particular *Staphylococcus aureus*, which is known to predominate the commensal bacteria of the skin.

In terms of immunology, the issue is one of immune response imbalance. Atopy is often described as an allergic manifestation (IgE mediated, dominance of cytokines IL-4, IL-5, IL-13) or Th2 response. The latter is all the more accentuated in the presence of "antigenic stimuli" of *Staphylococcus aureus*. Immunomodulation consists in returning immune homeostasis to a Th1/Th2 balance.

Innate immunity is the primary, rapid and nonspecific response of the immune response in mammals. The cell's first barriers of defense are comprised of Toll-like receptors (TLRs). Each TLR specifically recognizes pathogen-associated molecular patterns (PAMPs) such as nucleic acids (TLR3), peptides, surface proteins, lipoteichoic acid (TLR2), flagella (TLR5) and lipopolysaccharides (TLR4) arising from foreign microorganisms. A specific interaction between a motif (agonist) and a TLR triggers a cascade of complex reactions resulting in the transcription of NFκB, followed by production of pro-inflammatory and anti-inflammatory cytokines and of chemokines (Kang et al., 2006). Other resulting pharmacological consequences are the induction of antimicrobial peptides (AMPs), which have the ability to inhibit the growth of pathogens (bacteria, viruses, parasites) (Glaser, R. et al. 2005, Nat. Immunol. 6:57-64).

Atopic dermatitis is often accompanied by itching and pruritus, thus causing discomfort and annoyance in daily life (scratching, sleep loss, etc.). One of the causes of this inflammatory pathology is due to the activation of a G protein-coupled receptor called PAR2 (protease-activated receptor 2) (Steinhoff, M. et al. 2003 J Neurosci. 23:6176-6180). PAR2 is expressed on the surface of many cells, in particular keratinocytes, endothelial cells, colonic myocytes, enterocytes, enteric neurons and immune cells. Proteases (trypsin, tryptase), present in abundance in the epidermis, cleave the PAR2 at the N-terminal exposing a specific peptide which activates this same receptor (phenomenon of self-activation) (Vergnolle, N. 2009 Pharmacol. Ther. 123: 292-309). This process involves activation of the NFκB gene, followed by the induction of pro-inflammatory cytokines, thus triggering inflammation. In this context, the development of PAR2 antagonists and/or protease inhibitors has a high potential to treat the pathology of pruritus.

Psoriasis is also a cutaneous inflammatory disease with a chronic progression; it affects 2% of the population. Along with atopic dermatitis, psoriasis is one of the most common chronic cutaneous inflammatory diseases. It is characterized by abnormal growth of epidermal cells associated with an inflammatory reaction. The central mechanism of the inflammation phenomenon is related to the action of the immune system's T cells, predominantly Th1 cells (Wilsmann-Theis, D. et al., Eur J Dermatol., vol. 18(2) 172-180), which initiate and maintain the inflammatory process and stimulate the excessive proliferation of keratinocytes which then proceed through an accelerated and incomplete differentiation phase. Keratinocytes express receptors which make them sensitive to inflammatory signals and release pro-inflammatory mediators. Psoriatic inflammation is thus maintained by mutual stimulation of T cells and keratinocytes.

The disease must therefore be treated over the long term. There is thus a need and a high demand for therapeutic alternatives for these inflammatory dermatoses.

Mention may be made of patent document EP2018891 (Guéniche A., 2009) and the document by Guéniche A. et al., 2006 (European Journal of Dermatology, 16, 4, 380-384)

which describe the use of a bacterial extract of *Vitreoscilla filiformis* (*V. filiformis*) for the treatment of atopic dermatitis. Such an extract has the disadvantage of requiring the culture of said filamentous bacterium *V. filiformis* on a medium containing sulfur-free mineral water.

In this context, the present invention provides a solution to the treatment of these inflammatory disorders by the isolation, the characterization and the fractionation of a novel bacterium never before described.

For the first time, and in a surprising manner, the Applicant succeeded in isolating a strain belonging to a novel bacterial species from groundwater, wherein said novel bacterial strain (or bacterium) is named LMB64.

This bacterium LMB64, in addition to the fact of having been isolated, was characterized and defined as belonging to the class of Betaproteobacteria, subfamily of Neisseriaceae, and probably of a novel genus not yet defined. Analysis of the gene sequence coding for 16S ribosomal RNA (rRNA) made it possible to place this bacterium close to the genera *Chromobacterium, Paludimonas, Lutelia* and *Glubenkiana*, with which it shares 95% sequence similarity.

This nonpathogenic bacterium is Gram-negative and will be described in greater detail in the examples. This bacterium also has the characteristic of being nonfilamentous. Moreover, this bacterium has the advantage of being able to be cultured on a medium containing any type of water, and more particularly, ordinary water. As an example, in contrast to *V. filiformis*, the culture of bacterium LMB64 of the present invention does not require particular culture conditions and, more particularly, does not require a medium containing at least one sulfur-free type of mineral and/or thermal water. This represents a clear advantage in terms of both culture conditions and facilities and from an economic point of view.

The gene coding for 16S rRNA has been almost completely sequenced (1487 bp, corresponding to sequence SEQ ID No. 1). Bacterium LMB64 has a circular plasmid of 10948 bp. This plasmid was completely sequenced and the sequence is represented in sequence SEQ ID No. 2.

According to a first embodiment, the present invention relates to a nonpathogenic Gram-negative bacterium belonging to the class of Betaproteobacteria, subfamily of Neisseriaceae, whose nucleotide sequence of the gene coding for 16S rRNA includes or comprises the sequence SEQ ID No. 1, or any nucleotide sequence with at least 80%, preferably 85%, 90%, 95% and 98% identity with said sequence SEQ ID No. 1.

In a preferred manner, the present invention relates to a nonpathogenic Gram-negative bacterium belonging to the class of Betaproteobacteria, subfamily of Neisseriaceae, characterized in that the nucleotide sequence of the 16S rRNA gene of said bacterium includes or comprises the sequence SEQ ID No. 1.

In the context of the present invention, "percentage identity" between two nucleic acid sequences refers to a percentage of identical nucleotides between the two sequences to be compared, obtained after the best alignment (optimal alignment), wherein this percentage is purely statistical and the differences between the two sequences are distributed randomly and over their entire length. Comparisons of sequences between two nucleic acid sequences are normally made by comparing these sequences after having aligned them in an optimal manner, wherein said comparison may be made per segment or per "comparison window." The optimal alignment of the sequences for the comparison can be carried out, in addition to manually, by means of the local homology algorithm of Smith and Waterman (1981) [Ad. App. Math. 2:482], by means of the local homology algorithm of Needleman and Wunsch (1970) [J. Mol. Biol. 48:443], by means of the similarity search method of Pearson and Lipman (1988) [Proc. Natl. Acad. Sci. The USA 85:2444] or by means of computer software using these algorithms (GAP, BESTFIT, FASTA and TFASTA in the Wisconsin Genetics Software Package, Genetics Group Computer, 575 Science Dr., Madison, Wis., or the BLAST N or BLAST P comparison software).

The percentage identity between two nucleic acid sequences is determined by comparing these two aligned sequences in an optimal manner wherein the nucleic acid sequence to be compared may include additions or deletions in relation to the reference sequence for an optimal alignment between these two sequences. Percentage identity is calculated by determining the number of positions for which the nucleotide is identical between the two sequences, by dividing this number of identical positions by the total number of positions in the comparison window and by multiplying the result obtained by 100 to obtain the percentage identity between these two sequences.

For example, the "BLAST 2 sequences" program (Tatusova et aL, "Blast 2 sequences—a new tool for comparing protein and nucleotide sequences," FEMS Microbiol Lett. 174:247-250), available at http://wwvv.ncbi.nlm.nih.gov/gorf/b12.html, may be used with the default parameters (in particular for the parameters "open gap penalty": 5, and "extension gap penalty": 2; with the selected matrix being for example the "BLOSUM 62" matrix proposed by the program), with the percentage identity between the two sequences to be compared being calculated directly by the program. It is also possible to use other programs such as the "ALIGN" or "Megalign" software (DNASTAR).

According to another embodiment, the bacterium according to the invention includes at least one plasmid comprising sequence SEQ ID No. 2, or any sequence with at least 80%, preferably 85%, 90%, 95% and 98% identity with said sequence SEQ ID No. 2.

In a preferred manner, bacterium LMB64 includes at least one plasmid comprising sequence SEQ ID No. 2.

According to a preferred embodiment of the invention, bacterium LMB64 is characterized in that it is nonfilamentous.

Other characteristics of said bacterium LMB64 will be detailed below in the examples.

Moreover, bacterium LMB64 of the present invention has been deposited in accordance with the Budapest Treaty in the name of the Applicant with the Collection Nationale de Cultures de Microorganismes (CNCM), Institut Pasteur, Paris, on Apr. 8, 2010, under the reference I-4290.

Thus, one object of the invention is the bacterium deposited with the CNCM on Apr. 8, 2010, under the reference I-4290, or a homologue, a descendant or any other mutant.

The term "mutant" refers to any bacterium directly arising from strain I-4290 and may comprise natural mutations or recombinations, such as, for example, any recombination related to cell proliferation, cell division (mutation due to errors occurring during bacterial division or DNA replication) or any other mechanism of natural selection, such as the selection of mutants that are resistant or that become resistant to a given compound. Included among these mutants are any bacteria arising from strain I-4290 comprising one or more mutations in their genomic sequence (or that of their plasmid), in which the mutations were caused by radiation, by a virus, by transposons or by mutagenic chemicals.

According to a first embodiment of the invention, from a bacterial culture, the entire biomass may be isolated by various known methods such as, for example, by filtration, coagulation with an alcohol (ethanol, isopropanol, isobutanol), by drying on a cylinder with a scraped prelayer, etc., and then used in freeze-dried or heat-inactivated form.

According to another preferred embodiment, the invention relates in a general manner to a bacterial extract, also called a bacterial fraction, obtained from a suspension of bacteria as described above, namely bacterium LMB64.

The term "bacterial extract" refers to any extract or fraction of the bacterial biomass or any active fraction of said extract. For example, such an extract may be obtained from a culture of bacterium LMB64 wherein the preparation method comprises at least one step of lysis of the bacteria and one step of separation of the various fractions of which it is constituted by centrifugation or by filtration.

In a nonrestrictive manner, the extract according to the invention may consist of bacterial cells isolated from the culture medium which have been concentrated, for example by centrifugation; or concentrated bacterial cells which have undergone an operation in which the cell envelope has been ruptured by any means known to those persons skilled in the art, such as by the action of ultrasound or autoclaving; or the supernatant obtained by filtration.

An important step of the extract preparation method according to the invention consists of the elimination of the various intracellular components such as, for example, nucleic acids (chromosomal DNA, extrachromosomal circular DNA, plasmids), ribosomes and intracellular stored substances such as glycogen, starch and poly-β-hydroxybutyrate, etc.

In a preferred manner, the bacterial extract according to the invention is obtained after treatment of said bacterial suspension in such a way as to eliminate the intracellular components.

The result is that the extract according to the invention primarily includes components arising from the membrane, from the periplasmic space and/or from the extracellular space.

More particularly, said intracellular components comprise at least the nucleic acids.

In addition to the elimination of intracellular compounds, and as a nonrestrictive example, it is also easily possible for those persons skilled in the art to separate, after lysis of the bacteria and centrifugation, the components of the culture supernatant (hereafter fraction S0) and the components constituting the pellet (hereafter E0). For example, it may be suggested that the separation threshold between the constituents of S0 and E0 is around a molecular weight of 100 kDa. Consequently, the constituents of fraction S0 have, for the most part, a molecular weight less than 100 kDa, whereas the components of fraction E0 have, for the most part, a molecular weight greater than 100 kDa.

More particularly, it is thus possible by techniques known to those persons skilled in the art to extract and separate the biomolecules found in the culture supernatant (S0) from those mainly comprised of surface proteins and proteins located in the periplasmic space of the bacterium (E0).

According to one embodiment of the invention, the bacterial extract includes a fraction E0 comprising at least membrane proteins, periplasmic proteins and proteins arising from the flagellum.

Periplasmic proteins include proteins lodged in the periplasmic space of Gram-negative bacteria which may be released by osmotic shock or by incubation in a medium containing a chaotropic agent or detergents (Molecular Cloning: A Laboratory Manual, 3$^{rd}$ edition: Sambrook and Russell. CSHL Press).

Proteins arising from the flagellum include multimeric proteins of the flagellum or fragments of the flagellum. Methods for isolating and purifying whole bacterial flagella with detergents followed by ultracentrifugation separations (in the presence of a CsCl gradient) are described in the literature. In the invention, the examples of extraction methods made it possible to recover flagella fragments.

Membrane proteins include proteins that are anchored in the membrane and of which a part is exposed on the surface (outer membrane proteins, or Omp), proteins that are adhered to the surface of the membrane, lipoproteins and porins (Ward J B., Microbial adhesion to surfaces, 1980).

In a preferred manner, said membrane proteins consist of porins, OmpA, lipopolysaccharides and/or lipoproteins.

According to another embodiment of the invention, it may be preferred to use fraction S0.

More particularly, the bacterial extract according to the invention includes a fraction S0 comprising at least secreted peptides and proteins and secondary metabolites.

Secreted peptides and proteins include peptides and proteins that are naturally produced and secreted by bacterium LMB64 and which may be recovered by centrifugation or by filtration.

Secondary metabolites include the small molecules that bacterium LMB64 produces and secretes in the culture medium.

The presence of lipopolysaccharides within fraction S0 should be mentioned here. Indeed, lipopolysaccharides, although they are found primarily in fraction E0, are nevertheless also found in smaller quantities in fraction S0.

In an advantageous manner, fractions E0 and S0 may be combined in such a way as to obtain a fraction ES0 by leaving, for example, the culture medium to incubate and to react in basic medium (pH 9 to 11) for approximately 5 hours a temperature of 4° C., by centrifuging and by filtering at 0.2 μm in order to obtain a clear ES0 solution.

Bacterial extract ES0 is thus composed, among other things, of membrane proteins, lipopolysaccharides, periplasmic proteins, protein fragments of the flagellum and primary and secondary metabolites produced by the bacterium.

In a preferred way, extract ES0 has a protein profile comprising at least, according to the SDS-PAGE technique, twelve bands including three principal bands corresponding, respectively, to molecular weights (approximate molecular weights given in relation to molecular standards, notably provided by Bio-Rad Laboratories) ranging between:
  band 1: 30 kDa and 36 kDa, preferentially 34 kDa;
  band 2: 41 kDa and 45 kDa, preferentially 43 kDa;
  band 3: 47 kDa and 51 kDa, preferentially 49 kDa.

According to another embodiment of the invention, the bacterial extract includes a fraction ES0 comprising at least fraction E0 and fraction S0.

According to a preferred embodiment of the invention, the bacterial extract includes a fraction ES0 with a protein profile, obtained by SDS-PAGE, which includes three principal bands corresponding to molecular weights ranging between 30 kDa and 36 kDa, 41 kDa and 45 kDa, and 47 kDa and 51 kDa, respectively.

According to a preferred embodiment of the invention, the bacterial extract includes a fraction ES0 with a protein profile, obtained by SDS-PAGE, which includes three principal bands corresponding to molecular weights of 34 kDa, 43 kDa and 49 kDa, respectively.

According to another aspect, the invention describes a method for preparing a bacterial extract comprising the steps of:
a) culturing bacterium LMB64 in a suitable medium; and
b) eliminating the intracellular components.

According to another embodiment, the method according to the invention consists of a method for preparing a bacterial extract S0, wherein said method comprises the steps of:
a) culturing bacterium LMB64 in a suitable medium;
b) centrifuging said culture; and
c) recovering supernatant S0.

According to another embodiment, the method according to the invention consists of a method for preparing a bacterial extract E0, wherein said method comprises the steps of:
a) culturing bacterium LMB64 in a suitable medium;
b) centrifuging said culture and eliminating the supernatant;
c) treating the biomass resulting from step b) in such a way as to eliminate the intracellular components; and
d) recovering base E0.

In a preferred manner, step c) consists of ultrasonic treatment of the biomass resulting from step b) and then an initial centrifugation aimed at eliminating the pellet comprising said intracellular components and then a second centrifugation of the supernatant.

According to another embodiment, the method according to the invention consists of a method for preparing a bacterial extract E0, wherein said method comprises the steps of
a) culturing bacterium LMB64 in a suitable medium;
b) centrifuging said culture and eliminating the supernatant;
c) treating with ultrasound the biomass resulting from step b);
d) centrifuging said biomass treated with ultrasound and eliminating the biomass obtained;
e) centrifuging the supernatant resulting from step d); and
f) recovering the base E0.

It should be noted that the various methods described above are provided for illustration only and that any methods known to those persons skilled in the art may be used.

As will become apparent from the examples below, the Applicant has demonstrated, in addition to the activities expected for this type of extract, several novel activities never before described.

A first advantageous aspect of the invention, related to immunomodulation, rests on the modulation property of pro-inflammatory cytokines. More particularly, the use of a bacterium and/or an extract according to the invention significantly induces cytokines IL-10, IL-12 and TNF-α, which are preferentially involved in the Th1 immune response, and significantly inhibits cytokines IL-4 and IL-6. The result is the activation of Langerhans cells and a return to Th1/Th2 balance.

Furthermore, another observation demonstrated that the use of a bacterium and/or an extract according to the invention makes it possible to greatly decrease the expression of IgE receptors, which is of interest in that IgE potentiates allergic phenomena.

Another advantage of the invention rests on the fact that, as will be apparent from the examples, the use of a bacterium and/or an extract according to the invention induces the production of antimicrobial peptides such as, for example, peptides hBD-2, hBD-3, S1007A and LL-31.

More particularly, as mentioned above, an extract of bacterium *Vitreoscilla filiformis* (Guéniche A. et al., Eur J Dermatol 2006; 16:380) has been known with activity on TLR2, due to the presence of OmpA, and on TLR4, due to the presence of lipopolysaccharides. Because of the absence of flagella in the *V. filiformis* bacterium, the extract obtained from *V. filiformis* has no TLR5 activity.

For the first time, the Applicant describes a bacterial extract according to the invention which has, in addition to activity on TLR2 and TLR4, activity on TLR5.

The invention thus relates to the use of a bacterium and/or a bacterial extract such as described above as an activator of TLR2, TLR4 and TLR5.

In a preferred manner, said bacterial extract activator of TLR2, TLR4 and TLR5 consists of an extract comprising all or part of the proteins arising from the flagellum. In this case, as an example, said extract is preferentially extract E0 or extract ES0.

Said TLR5 activation activity is of significant interest in that TLR5 are known to induce certain antimicrobial peptides such as psoriasin (S100A7) and hBD-2 (Glaser et al., Journal of Investigative Dermatology (2009) 129, 641-649). Moreover, TLR5 agonists act in synergy with those of TLR2 and TLR4, thus making it possible to potentiate the production of antimicrobial peptides. It has been shown that by blocking TLR5 with an antibody, the latter are produced little or not at all.

This aspect is thus particularly innovative in terms of immunomodulation applications for the bacterium and/or the extracts according to the invention.

Furthermore, in an unexpected manner, the Applicant has also demonstrated, in contrast to the bacterial extracts described to date, antagonistic activity toward PAR2. This activity is of significant interest in the context of anti-inflammatory treatments.

The invention thus relates, quite particularly, to the use of a bacterium and/or a bacterial extract such as described above as a PAR2 antagonist.

In a preferred manner, said PAR2 antagonist bacterial extract consists of extract S0 or extract ES0.

PAR2 is overexpressed in endothelial cells, colonic myocytes, enterocytes, enteric neurons, immune cells and keratinocytes. Proteases (trypsin, tryptase) present in abundance in the environment cleave the PAR2 at the N-terminal exposing a specific peptide which activates this same receptor (phenomenon of auto-activation). Consequently, this activates the production of pro-inflammatory cytokines and triggers inflammation (Vergnolle, N., 2009 Pharmacol. Ther. 123:292-309). This phenomenon is observed in the wild mouse but does not appear in the KO mouse (PAR2 deficient). Treatment with an antiprotease and/or a PAR2 antagonist makes it possible to avoid this inflammation phenomenon.

The combination and the synergy of all these activities give this bacterium LMB64, or any extract arising from this same bacterium, a high potential to treat inflammatory diseases and, quite particularly, inflammatory diseases in which PAR2 is involved and/or in which the immune system is weakened, disturbed or unbalanced.

The invention thus relates to the use of a bacterium such as described above and/or a bacterial extract arising from said bacterium for the preparation of a composition intended for the treatment and/or the prevention of dermatological inflammatory disorders.

In a preferred manner, said dermatological inflammatory disorders consist of atopic dermatitis, pruritus, eczema and psoriasis.

According to another embodiment, the invention of the present patent application relates to a composition comprising, as an active ingredient, at least one bacterium and/or one bacterial extract according to the invention.

The invention thus relates, in a preferred manner, to a cosmetic or dermatological composition.

The composition according to the invention relates to the treatment of dermatological inflammatory disorders.

In a preferred manner, said dermatological inflammatory disorders consist of atopic dermatitis, pruritus, eczema and psoriasis.

The composition according to the invention may in particular contain additives and formulation aids such as emulsifiers, thickeners, gelling agents, water binders, spreading agents, stabilizers, colorants, fragrances and preservatives.

The cosmetic or dermatological composition according to the invention further comprises one or more typical dermatologically-compatible excipients.

The composition according to the invention may be prepared in the form of a water-in-oil (W/O) or oil-in-water (O/W) emulsion, a multiple emulsion such as, for example, a water-in-oil-in-water (W/O/W) or oil-in-water-in-oil (O/W/O) emulsion, a microemulsion or in the form of a hydrodispersion or a lipodispersion, a gel or an aerosol.

The dermatologically or cosmetically compatible excipients may be any excipient among those known to those persons skilled in the art in order to obtain a composition for topical application in the form of a milk, a cream, a balm, an oil, a lotion, a gel, a foaming gel, a pomade, a spray, etc.

In addition to dermatological and cosmetic compositions, the invention also relates to pharmaceutical compositions for a use as drug.

The invention thus relates to a pharmaceutical composition further comprising a pharmaceutically acceptable carrier.

In the present description, "pharmaceutically acceptable carrier" refers to a compound or a combination of compounds made part of a pharmaceutical composition that do not cause secondary reactions and that, for example, facilitate the administration of the active compounds, increase their lifespan and/or effectiveness in the body, increase their solubility in solution or improve their preservation. Said pharmaceutically acceptable carriers are well known and will be adapted by those persons skilled in the art according to the nature and the mode of administration of the active compounds selected.

Preferably, said compounds may be administered systemically by intramuscular, intradermal, intraperitoneal or subcutaneous route, or by oral route. The composition comprising the antibodies according to the invention may be administered in several doses, spread out over time.

Their optimal modes of administration, dosing schedules and galenic forms may be determined according to criteria generally considered in the establishment of a treatment adapted to a patient such as, for example, the age or the weight of the patient, the seriousness of the patient's general health, tolerance to the treatment and side effects noted.

The invention will be better understood upon consideration of the examples below which illustrate the invention without limiting its scope.

EXAMPLE 1

Selection and Characterization of Bacterium LMB64

Bacterium AV13 was isolated from groundwater.

Figure 1:
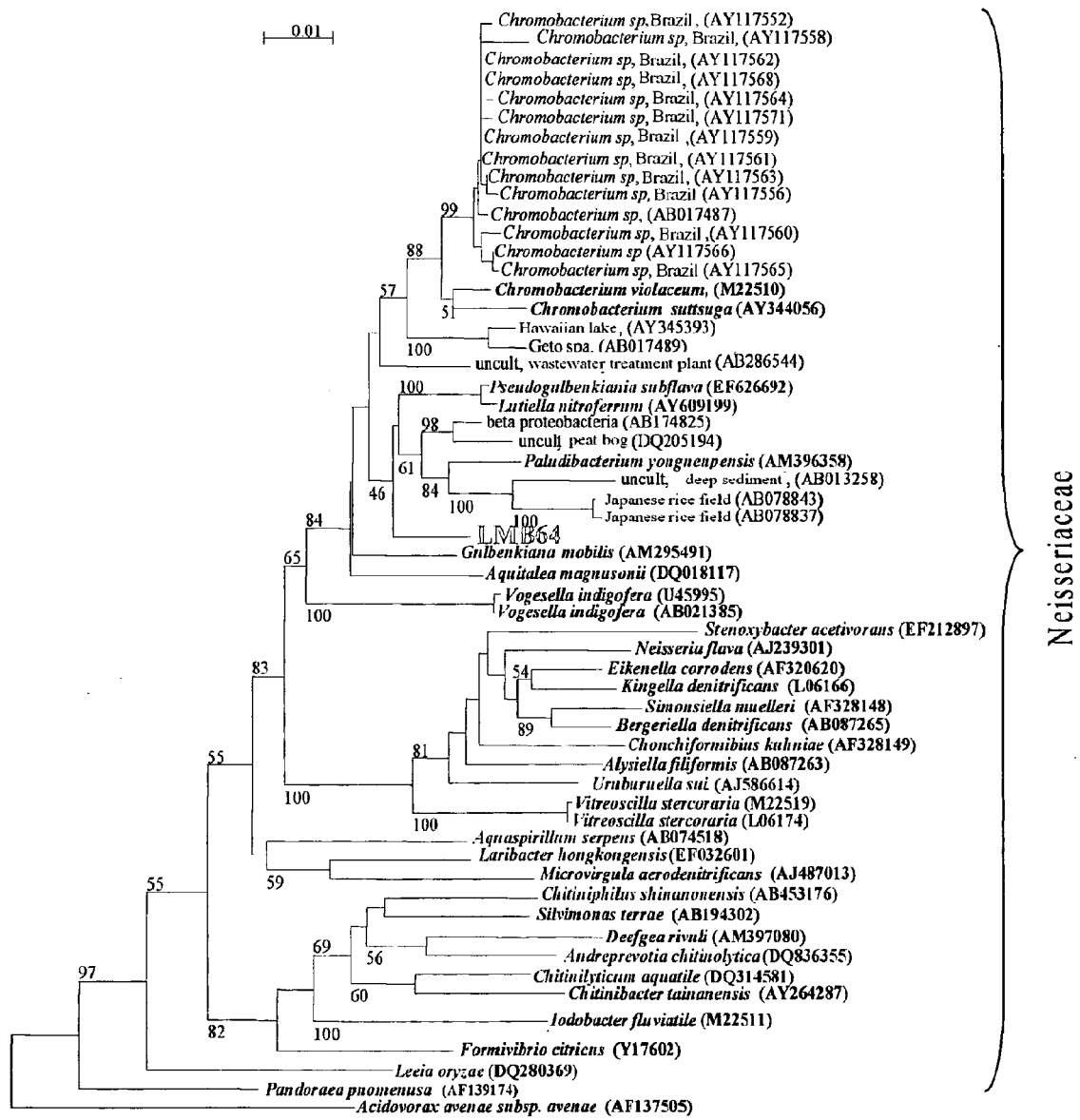
FIG. 1 illustrates the phylogenetic position of the sequence coding for the 16S rRNA of strain LMB64. The sequences appearing on this tree are sequences from the GenBank database closest to the sequence of LMB64.

The taxonomic position of novel bacterium LMB64 is proposed in FIG. 1.

Figure 2A:
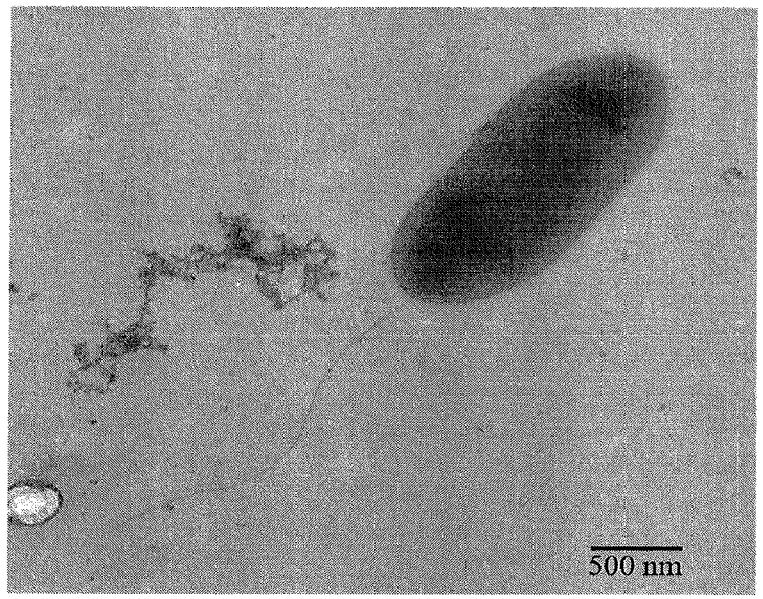
FIGS. 2A and 2B present images of bacterium LMB64 under the transmission electron microscope (A) and the scanning electron microscope (B).
Figure 2B:
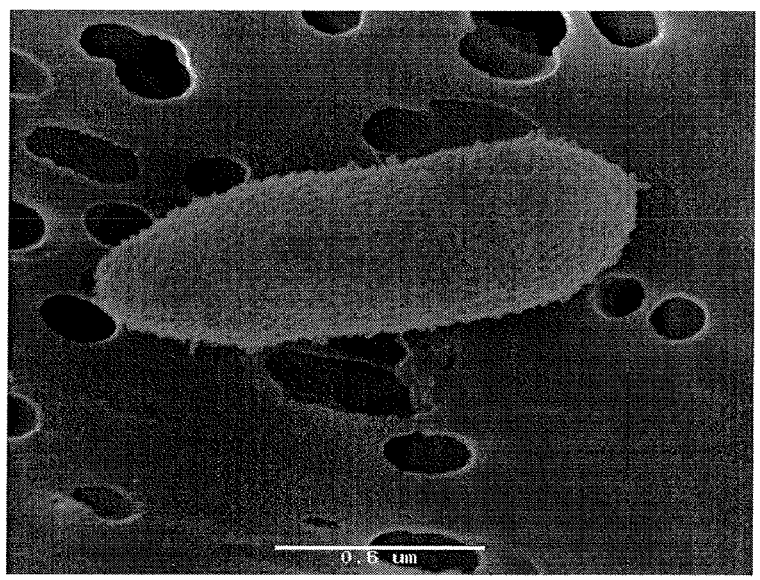

More particularly, bacterium LMB64 is rod-shaped with a length of roughly 2.3 μm (±0.3) and a width of roughly 1.0 μm (±0.1). A distinctive characteristic of this bacterium is the presence of a polar flagellum (FIGS. 2A and 2B). As can also be seen in these images, bacterium LMB64 is a non-filamentous bacterium.

As mentioned above, bacterium LMB64 has a circular plasmid of roughly 11 kpb. This plasmid was completely sequenced (SEQ ID No. 2).

The gene coding for 16S rRNA was also sequenced (SEQ ID No. 1). The bacterium was cultured in a fermentor in a synthetic medium. The growth rate is higher when the medium has a low concentration of carbon substrates.

The culture media tested are R3, MS-glucose and LB media whose compositions are described below in tables 1a, 1b and 1c, respectively.

TABLE 1a

| COMPOSITION OF R3 MEDIUM | |
|---|---|
| Yeast extract | 1 g/l |
| Difco proteose peptone | 1 g/l |
| Casamino acids | 1 g/l |
| Glucose | 1 g/l |
| Soluble starch | 1 g/l |
| Sodium pyruvate | 0.5 g/l |
| $K_2HPO_4$ | 0.6 g/l |
| $MgSO_4, 7H_2O$ | 0.1 g/l |

TABLE 1b

| COMPOSITION OF MS-GLUCOSE MEDIUM | |
|---|---|
| Glucose | 6.0 g/l |
| Citric acid | 0.84 g/l |
| $MgSO_4, 7H_2O$ | 0.25 g/l |

TABLE 1b-continued

COMPOSITION OF MS-GLUCOSE MEDIUM

| | |
|---|---|
| NH$_4$Cl | 1.06 g/l |
| Anhydrous K$_2$HPO$_4$ | 8.75 g/l |
| Pyruvic acid sodium salt | 0.5 g/l |
| Zinc sulfate, 7H$_2$O | 4 mg/l |
| Cobalt chloride, 6H$_2$O | 3.5 mg/l |
| Sodium molybdate, 2H$_2$O | 3.5 mg/l |
| Manganese sulfate, 1H$_2$O | 5 mg/l |
| Boric acid | 2 mg/l |
| Concentrated hydrochloric acid | 50 mg/l |
| Copper sulfate, 5H$_2$O | 4 mg/l |
| Iron chloride, 6H$_2$O | 27 mg/l |

TABLE 1c

COMPOSITION OF LB MEDIA

| | |
|---|---|
| Tryptone | 10 g/l |
| Yeast extract | 5 g/l |
| NaCl | 5 g/l |

The growth rates of bacterium LMB64 as a function of culture medium are presented in table 2 below.

TABLE 2

| | Growth rate (/h) |
|---|---|
| LB | 0.25 (±0.05) |
| LB (½ dilution) | 0.46 (±0.11) |
| LB (⅕ dilution) | 0.60 (±0.14) |
| LB (¹⁄₁₀ dilution) | 0.69 (±0.15) |
| MS-glucose | 0.13 (±0.04) |
| R3 | 0.62 (±0.14) |

Figure 3:
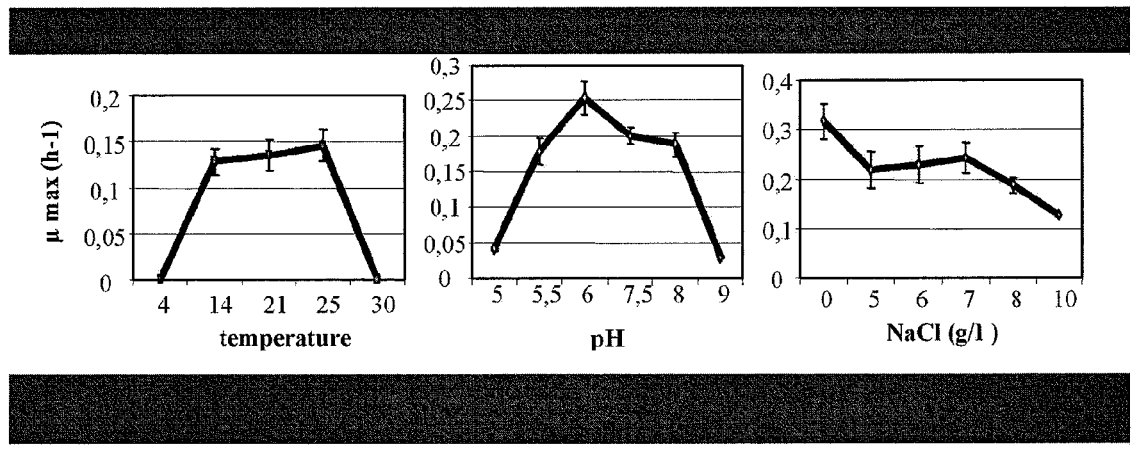
FIG. 3 presents growth optima determined as a function of the temperature, pH and salinity of the R3 culture medium.
Figure 3:

The growth optima were determined as a function of the temperature, pH and salinity of the R3 culture medium (FIG. 3).

The sources of carbon assimilable by the bacterium were characterized using an API 50CH gallery (incubation temperature: 25° C.). The results are summarized in table 3 below.

TABLE 3

| | Incubation time | |
|---|---|---|
| | 4 days | 5 days |
| 1. Glycerol | | |
| 2. Erythritol | | |
| 3. D-arabinose | | |
| 4. L-arabinose | | |
| 5. D-ribose | | |
| 6. D-xylose | | |
| 7. L-xylose | | |
| 8. D-adonitol | | |
| 9. Methyl-β-D-xylopyranoside | | |
| 10. D-galactose | | |
| 11. D-glucose | + | + |
| 12. D-fructose | + | + |
| 13. D-mannose | | |
| 14. L-sorbose | | |
| 15. L-rhamnose | | |
| 16. Dulcitol | | |
| 17. Inositol | l | + |
| 18. D-mannitol | | |
| 19. D-sorbitol | | |
| 20. Methyl-α-D-mannopyranoside | | |
| 21. Methyl-α-D-glucopyranoside | | |
| 22. N-acetylglucosamine | | |
| 23. Amygdaline | | |

TABLE 3-continued

| | Incubation time | |
|---|---|---|
| | 4 days | 5 days |
| 24. Arbutin | | |
| 25. Esculin/iron citrate | | |
| 26. Salicin | | |
| 27. D-cellobiose | | |
| 28. D-maltose | l | + |
| 29. D-lactose (bovine origin) | | |
| 30. D-melibiose | | |
| 31. D-sucrose | + | + |
| 32. D-trehalose | l | + |
| 33. Inulin | | |
| 34. D-melezitose | | |
| 35. D-raffinose | | |
| 36. Starch | | |
| 37. Glycogen | | |
| 38. Xylitol | | |
| 39. Gentiobiose | | |
| 40. D-turanose | l | + |
| 41. D-lyxose | | |
| 42. D-tagatose | | |
| 43. D-fucose | | |
| 44. L-fucose | | |
| 45. D-arabitol | | |
| 46. L-arabitol | | |
| 47. Potassium gluconate | | |
| 48. Potassium 2-ketogluconate | | |
| 49. Potassium 5-ketogluconate | | |

+: usable substrate,
l: low use

The enzymatic activities demonstrated on the API ZYM gallery are: alkaline phosphatase, esterase (C4), esterase/lipase (C8), leucine arylamidase, valine arylamidase, acid phosphatase, naphthol-AS-BI-phosphohydrolase, and α-glucosidase.

Bacterium LMB64 is sensitive to all the antibiotics tested as seen in table 4 below.

TABLE 4

| | Zone of inhibition diameter (mm) | | | Inhibitory |
|---|---|---|---|---|
| Antibiotics tested | R3 | LB ½ | LB ⅕ | activity |
| Ampicillin (10 μg) | 29 | 28 | 29 | + |
| Chloramphenicol (30 μg) | 29 | 26 | 24 | + |
| Ciprofloxacin (5 μg) | 38 | 34 | 34 | + |
| Kanamycin (30 μg) | 27 | 30 | 27 | + |
| Penicillin (6 μg) | 21 | 26 | 20 | + |
| Polymyxin B (50 μg) | 11 | 15 | 13 | + |
| Rifampicin (30 μg) | 20 | 19 | 15 | + |
| Tetracycline (30 μg) | 30 | 25 | 20 | + |
| Streptomycin (10 μg) | 25 | 25 | 24 | + |
| Vancomycin (30 μg) | 20 | 21 | 21 | + |

EXAMPLE 2

Method for Extracting Fractions E0, S0 and ES0

Preculture: Strain AV13 is inoculated in an Erlenmyer flask containing 250 ml of MS glucose pyruvate medium (see table 5 below), followed by incubation under stirring for roughly 40 hours at 30° C. (pH 7) and 200 rpm until an OD$_{600}$≈1.5 is obtained.

TABLE 5

MS Glucose Pyruvate

| | |
|---|---|
| Citric acid | 0.84 g |
| MgSO$_4$, 7H$_2$O | 0.25 g |
| NH$_4$Cl | 1.06 g |
| Anhydrous K$_2$HPO$_4$ | 8.75 g |
| Pyruvic acid sodium salt | 0.5 g |
| Oligo mix | 1 ml |
| ddH$_2$O qsp | 1000 ml |
| Verify pH | 7 |
| Autoclave | 121° C. 30 min |
| After autoclaving add: | |
| 20% glucose | 30 ml |

OLIGO MIX

| | |
|---|---|
| Dissolve in 100 ml of distilled water: | |
| Zinc sulfate, 7H$_2$O | 4 g |
| Cobalt chloride, 6H$_2$O | 3.5 g |
| Sodium molybdate, 2H$_2$O | 3.5 g |
| Manganese sulfate, 1H$_2$O | 5 g |
| Boric acid | 2 g |
| Concentrated hydrochloric acid | 50 g |
| Copper sulfate, 5H$_2$O | 4 g |
| Dissolve in 50 ml of distilled water: | |
| Iron chloride, 6H$_2$O | 27 g |
| ddH$_2$O qsp | 1000 ml |

Culture: The preculture is then inoculated in a fermentor (Applikon) containing 3.71 of MS pyruvate medium+114 ml of 20% glucose solution. A temperature sensor regulates the temperature preferably near 30° C. An oxygen sensor (AppliSens) is used to maintain the concentration of dissolved oxygen in the medium at 18-25%. A pH sensor (AppliSens) is used to maintain the pH at 7 by the addition of 10% NH$_4$OH via a fixed flow-rate pump. A Wedgewood Analytical sensor is used to monitor changes in optical density in real time. The culture is programmed in fed-batch mode; via a variable flow-rate pump the culture is supplied with 20% glucose solution. Fermentation is stopped when OD$_{600}$≈22-26, in general after roughly 30 hours.

Extraction S0: The supernatant is separated from the biomass by centrifugation for 1 hour at 4° C. and 4000 g.

Extraction E0: The wet biomass is taken up in NaCl solution (1 M). After centrifugation for 15 minutes at 4° C. and 9000 g, the supernatant is discarded and the pellet is taken up in 1 M NaCl solution. The sample tube is then plunged into a cooled ultrasonic bath at a power setting of 50-60 W for several minutes. After centrifugation for 30 minutes at 4° C. and 6000 g, the pellet is discarded and the supernatant is recovered. Two volumes of cold ethanol are added and the suspension is left overnight at 4° C. After centrifugation for 30 minutes at 4° C. and 6000 g, the supernatant is discarded and the pellet is taken up in 25 mM Tris buffer, pH 8.8.

Extraction ES0: The culture is brought to basic pH (pH 9-11) with a base buffer. The next step is incubation under stirring for 5 hours at a temperature of 4° C. After centrifugation, the supernatant is prefiltered to eliminate remaining biomass debris and then filtered on a 0.2 µm filter. A clear yellow solution is obtained (ES0).

Proteins are assayed according to the DC Protein Assay Kit II (Bio-Rad) protocol. Sugars are assayed in glucose equivalent according to the phenol/sulfuric acid method (Dubois, M. et al., 1956).

As an example, table 6 below presents certain specific characteristics of extract ES0 as obtained under the conditions described above.

TABLE 6

| | Test batch | Preclinical batch 1 |
|---|---|---|
| Organoleptic characteristics | Homogeneous and translucent yellow-orange liquid Density near that of water | |
| pH (in the presence of base buffer) | 10.0 | 10.2 |
| Dry residue (thermobalance) | 5.9% | 5.1% |
| Protein profile (SDS-PAGE) | 12 detectable bands (including 3 principal bands roughly 34 kDa, 43 kDa and 49 kDa in size, respectively) | |
| Total protein assay (µBCA) | 2.9 mg/ml | 3.0 mg/ml |

It is clearly understood that the data above are presented here only for illustrative purposes.

More precisely, the data relate to a protein profile obtained by SDS-PAGE exhibiting three principal bands.

SDS-PAGE Protocol:

Extract ES0 is taken up in buffer (20 mM Tris-HCl, pH 8.0; 1 mM EDTA; 2.5% SDS and 0.01% bromophenol blue) and 1 M DTT (1,4-dithiothreitol). The sample and the mixture of molecular weight markers (WesternC, Bio-Rad) were deposited respectively in wells of an 8-16% SDS-PAGE acrylamide gel (GeBaGel, Gene Bio-Application). The migration buffer contains 2.5 mM Tris, 19.2 mM glycine and 0.01% SDS (w/v). Migration is allowed to proceed under a constant voltage of 160 V for approximately 1 hour (GeBaGel system). The protein bands were then stained with Coomassie Blue (Instant Blue, Expedeon). Sizes were calculated in relation to known standards (STD).

Figure 12:
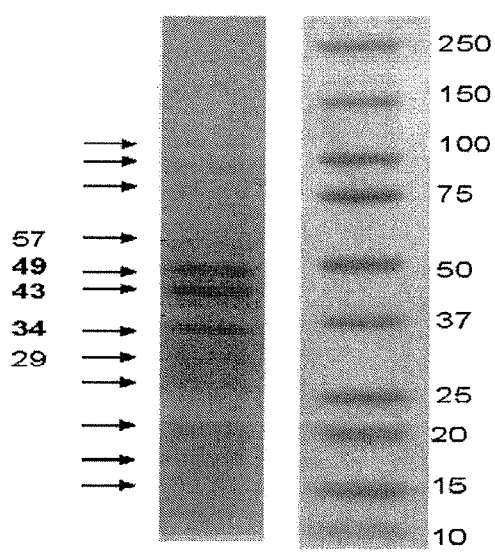
FIG. 12 consists of an SDS-PAGE gel of extract ES0.

The gel obtained is presented in FIG. 12.

According to one embodiment of the invention, these three bands have molecular weights of approximately 34 kDa, 43 kDa and 49 kDa, respectively.

EXAMPLE 3

Demonstration of the Pharmacological Activities of Fractions E0 and ES0

Langerhans cells (LC) are generated in vitro from human monocytes isolated from Buffy-Coat pouches from the French National Blood Service (Etablissement Français du Sang (EFS) Pyrénées Méditerranée): isolation on a Ficoll gradient (Lymphocyte Separation Medium, density 1.077 g/ml) and purification by magnetic immunoselection (Miltenyi Biotec); LC differentiation is carried out for 6 days in the presence of a cytokine cocktail (GM-CSF/IL-4/TGFβ). LC distributed on 24-well plates in RPMI-5% FCS culture medium are incubated for 24 hours with extract ES0.

Surface molecules are analyzed by flow cytometry (FACSCalibur, BD Biosciences) with triple or quadruple staining: CD1a/CD54/CD80/CD83/CD86/FcεRI; cytokines secreted in the culture supernatants are analyzed with the Cytometry Bead Array (cat. no. 550749, BD) in flow cytometry: IL-6, IL-8, TNF, IL-4, IL-10, IL-12.

3.1 Induction of Key Cytokines for Th1 Polarization

Figure 4:
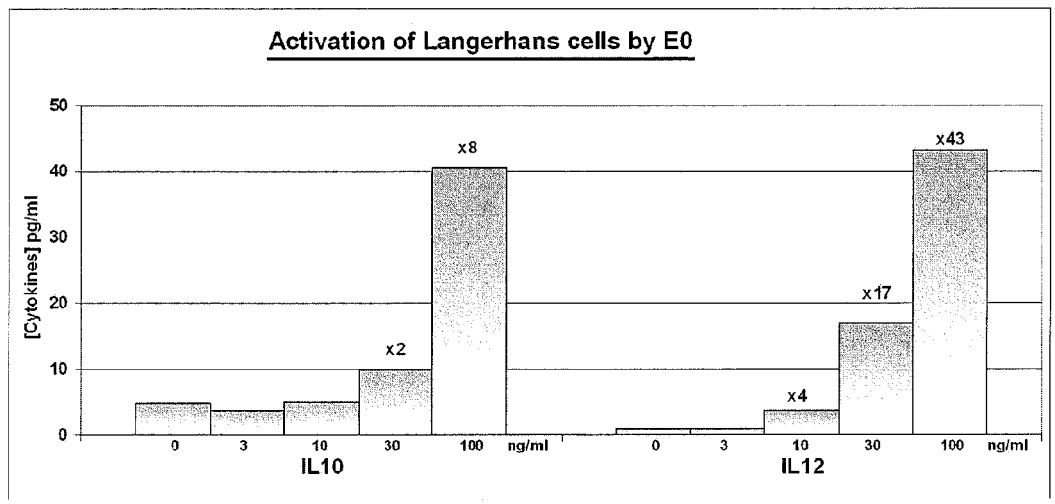
FIG. 4 illustrates induction of cytokines IL-10 and IL-12 by extract E0 (dose-dependent effect).
Figure 4:

Extract E0 induces according to a dose-dependent effect the expression of cytokines IL-10 and IL-12 by Langerhans cells (FIG. 4). These cytokines promote the induction of TH1 polarity of naive T lymphocytes.

3.2 Langerhans Cell Maturation and IgE Receptor (FcεRI) Inhibition

Figure 5:
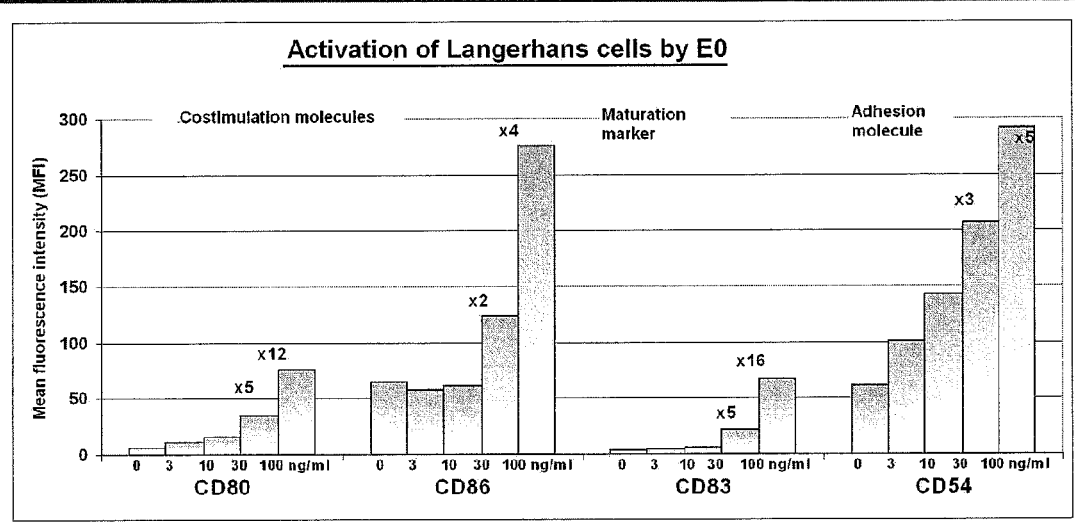
FIG. 5 illustrates induction of surface molecules CD80, CD86, CD83 and CD54 by extract E0 (dose-dependent effect).
Figure 6:
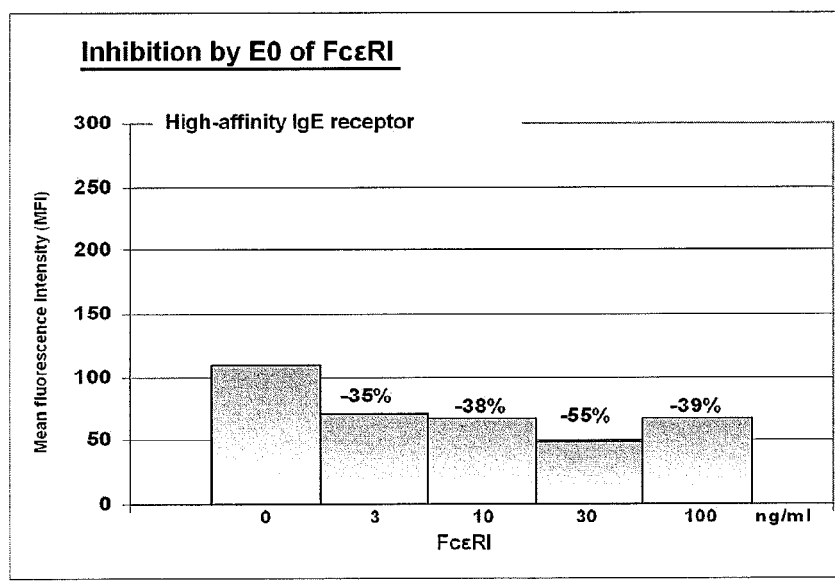
FIG. 6 illustrates inhibition of IgE receptors by extract E0.

Extract E0 induces the maturation of Langerhans cells observed by dose-dependent induction of surface molecules CD80, CD86, CD83 and CD54 (FIG. 5). Similarly, extract E0 inhibits the expression of IgE receptors (FcεRI) according to a dose-dependent effect (FIG. 6).

3.3 Activation of Toll-Like Receptors (TLRs)

The TLR activity of ES0 was evaluated on TLR2, TLR4 and TLR5 using the model of HEK293 cells cotransfected by the gene for TLR2, TLR4 or TLR5 and by the reporter gene NFκB-sAP (secreted alkaline phosphatase). The binding of a ligand to its TLR leads to the activation of the transcription factor NFκB; the sAP gene is placed under the control of a promoter that can be induced by NFκB. This reporter gene makes it possible to monitor cell signaling via TLRs: the release of sAP induced by ES0 and measured by colorimetric assay makes it possible to determine the activity of this active ingredient as a TLR2, TLR4 or TLR5 agonist.

The study was carried out on the following human embryonic kidney (HEK293) cell lines:
HEK-Blue™-2 cells for TLR2,
HEK-Blue™-4 cells for TLR4,
HEK-Blue™-5 cells for TLR5, These cell lines were maintained in HEK-Blue™ Selection 10% FCS culture medium and then distributed in 96-well plates in HEK-Blue™ Detection medium in the presence of ES0 for 18 hours. The plates are read using calorimetry at 620 nm 3.3.1 Activation of TLR2

Figure 7:
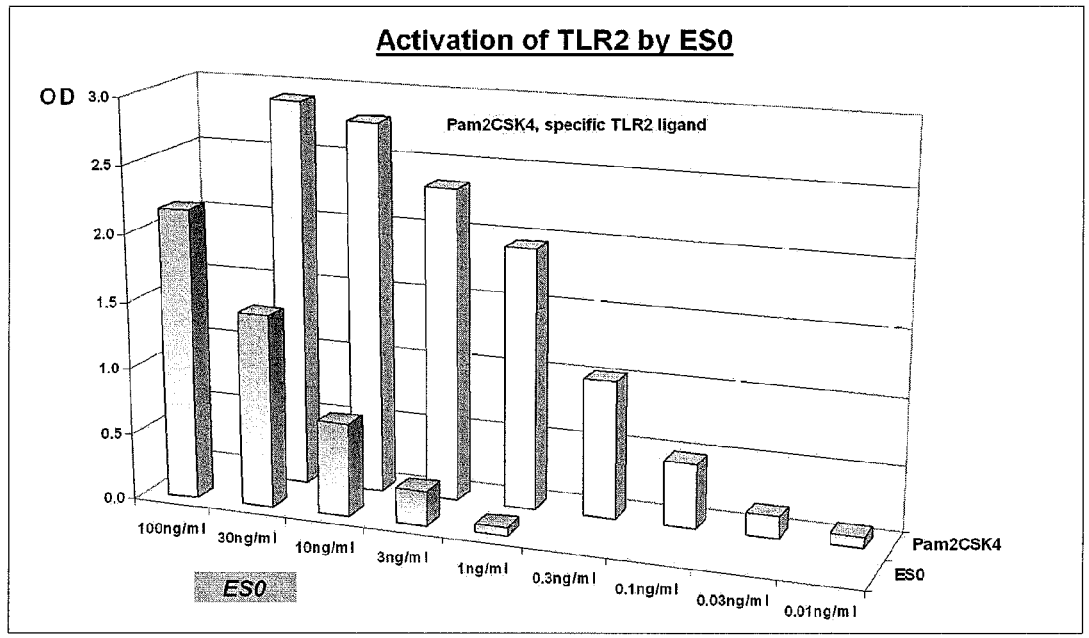
FIG. 7 illustrates activation of TLR2 by extract ES0.

Extract ES0 induces the activation of TLR2 according to a dose-dependent effect with a maximum activity at 100 ng/ml (FIG. 7).

3.3.2 Activation of TLR4

Figure 8:
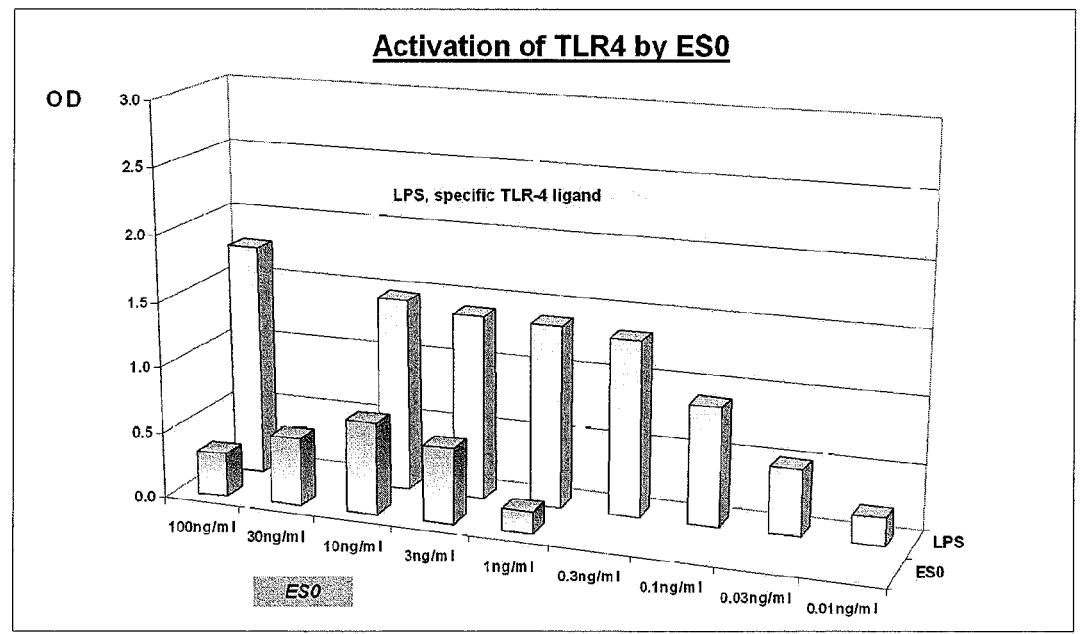
FIG. 8 illustrates activation of TLR4 by extract ES0.

Extract ES0 induces the activation of TLR4 with a maximum activity at 10 ng/ml (FIG. 8).

3.3.3 Activation of TLR5

Figure 9:
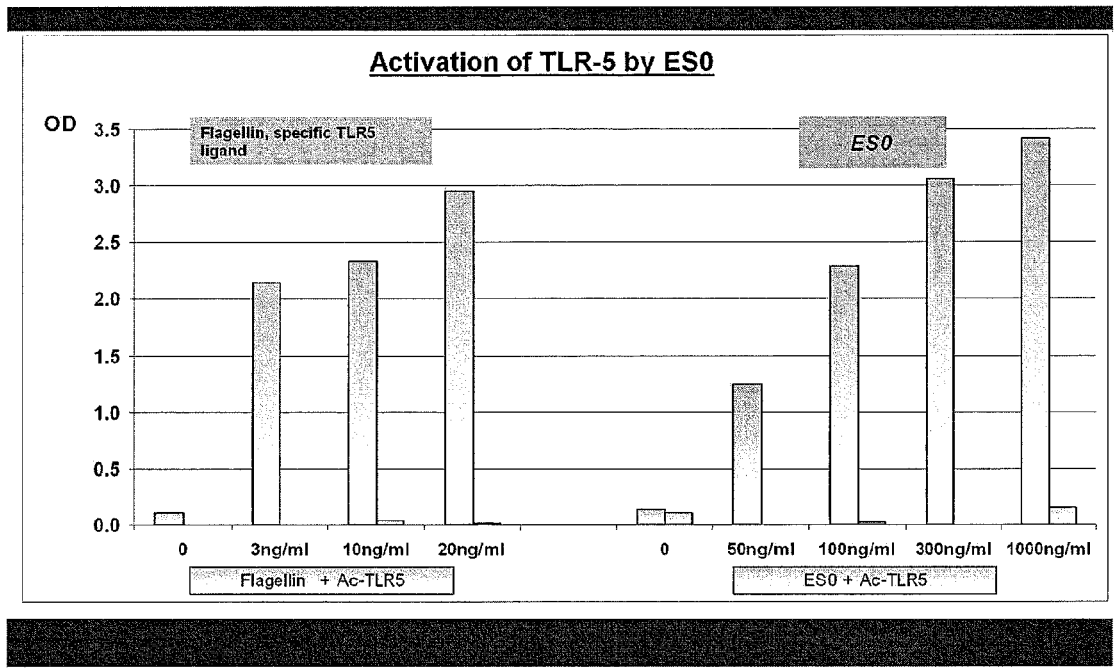
FIG. 9 illustrates activation of TLR5 by extract ES0.

Extract ES0 induces the activation of TLR5 in a dose-dependent manner. This activity is inhibited in the presence of anti-TLR5 antibody, demonstrating the activation specificity of extract ES0 on TLR5 (FIG. 9).

3.4 Inhibition of Protease-activated Receptor 2 (PAR2)

The inhibition of protease-activated receptors by extract ES0 is evaluated on human keratinocytes from a cell line (HaCaT) by measuring the intracellular calcium influx induced after specific stimulation of PAR2 with stratum corneum tryptic enzyme (SCTE). The fluorescent probe Fluo-4/AM is used: its esterified form facilitates its penetration by passive diffusion in the cell; only the deesterified form bound to calcium ions is excitable under 485 nm fluorescence and emits at 535 nm.

The fluorescent probe is incorporated for 30 minutes in cells inoculated in 96-well plates and then extract ES0 is incubated for 30 minutes. Calcium flow is measured well by well in real time according to kinetics before and after injection of SCTE. The plates are read using a Mithras LB940™ reader (Berthold Technologies®).

Figure 10:
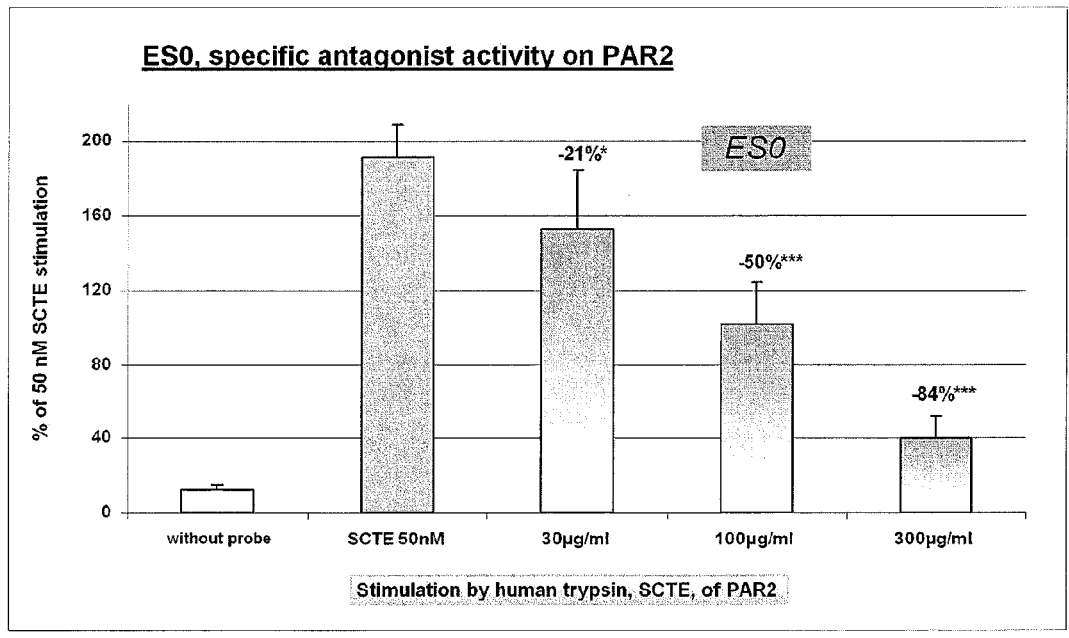
FIG. 10 illustrates specific PAR2 antagonist activity by extract ES0.

Extract ES0 inhibits in a dose-dependent manner activation of PAR2 induced by human SCTE (FIG. 10).

3.5 Modulation of Targets of Atopic Dermatitis on Keratinocytes

The study was carried out on normal human epidermal keratinocytes (NHEK, K-SFM culture medium) in the context of the induction of an atopic dermatitis phenotype. The activity of ES0 was studied on keratinocytes exhibiting an atopic dermatitis phenotype after stimulation for 24 hours with Poly I:C+IL-4+IL-13+TNF-α and analyzed by PCR array on the expression of a panel of 32 selected genes.

On keratinocytes, extract ES0 inhibited according to a dose-dependent effect 15 targets among the mediators involved in atopic dermatitis pathology, as can be seen clearly in table 7 below (the results indicating for each target gene the percentage of inhibition obtained).

TABLE 7

| | | ES0 | | | Dexamethasone |
|---|---|---|---|---|---|
| | | 10 µg/ml | 30 µg/ml | 60 µg/ml | 2 µM |
| Cyto-kines | TSLP | 56% | 75% | 92% | 91% |
| | IL-1α | 35% | 46% | 59% | 54% |
| | IL-18 | 27% | 44% | 65% | 44% |
| | IFN-β1 | 66% | 82% | 90% | 49% |
| Chemo-kines | IL-8 | 37% | 55% | 88% | 75% |
| | MIP-1α | 10% | 43% | 75% | 76% |
| | RANTES | 15% | 44% | 65% | 12% |
| | MCP-3 | 43% | 63% | 88% | Pro 20% |
| | TARC | 58% | 64% | 39% | Pro 20% |
| | MIP-3α | 41% | 61% | 80% | 40% |
| | MDC | 16% | 44% | 58% | 45% |
| | Skinkine | 28% | 32% | 39% | 59% |
| Recep-tors | IL-4-R | 30% | 45% | 69% | 75% |
| | RARRES3 | 30% | 47% | 63% | 28% |
| | TLR3 | 22% | 50% | 60% | pro 29% |

3.6 Induction of Antimicrobial Peptides

The activity of extract ES0 on the expression of antimicrobial peptides and proteins is studied on the HaCaT keratinocyte cell line: after 3 hours of treatment in the presence of ES0, the cells are recovered for an analysis of the expression of antimicrobial targets by quantitative RT-PCR; total RNA are extracted and assayed; after reverse transcription of mRNA into cDNA, the quantitative PCR amplification step is carried out in 96-well plates on an iCycler quantitative PCR system (Bio-Rad). The results obtained are expressed as the relative quantity (RQ) of mRNA after treatment by ES0 in relation to the control without the active ingredient. IL-1β is used in parallel as a reference positive inducer of antimicrobial peptide expression. Expression of the gene of interest is considered regulated when RQ≥2 (induction) or RQ≤0.5 (inhibition).

Figure 11:
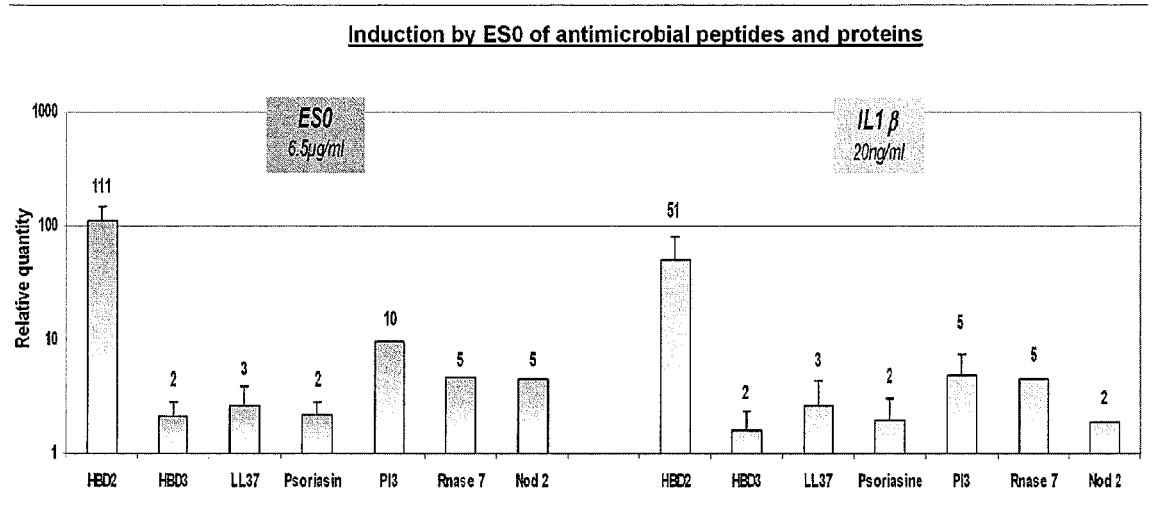
FIG. 11 illustrates induction of antimicrobial peptides and proteins by extract ES0.

Extract ES0 induces the expression of antimicrobial peptides and proteins hBD2, hBD3, S1007A, LL37, P13, RNase 7 and NOD2 (FIG. 11).

EXAMPLE 4

Formulation of a "Body and Face" Cream Comprising Bacterial Extract ES0

Extract ES0: 0.1-5%
Evening primrose oil: 1-3%
Glycine: 0.1-0.4%
Ceramides: 0.1-0.3%
Humectants: 5-20%
Emulsifier: 2-7%
Capric/caprylic triglycerides: 1-10%
Preservatives
Water qsp 100%

EXAMPLE 5

Formulation of a "Body and Face" Cleansing Gel Comprising Bacterial Extract ES0

Extract ES0: 0.1-5%
Evening primrose oil: 0.5-2%
Glycine: 0.1-0.4%
Ceramides: 0.1-0.4%
Surfactants: 10-20% in active matter
Humectants: 5-15%
Preservatives
Water qsp 100%

The invention claimed is:

1. A cosmetic or dermatological composition comprising effective amounts of a fractionated bacterial extract and a preservative,
   wherein the fractionated bacterial extract is obtained from a Gram-negative non-filamentous bacterium belonging to the class of Betaproteobacteria, subfamily of Neisseriaceae which nucleotide sequence of the 16S rRNA gene comrprises SEQ ID NO: 1,
   and wherein the fractionated bacterial extract is prepared by a method comprising incubating and reacting said bacterium in a basic medium of pH 9 to 11 for a suitable time, and removing intracellular components of the bacterium therefrom.

2. The composition according to claim 1, wherein said bacterium comprises at least one plasmid comprising SEQ ID NO: 2, or any sequence with at least 80% identity with said SEQ ID NO: 2.

3. The composition according to claim 1 wherein said bacterium has been deposited under deposit number 1-4290 in the Collection Nationale de Cultures de Microorganisms (CNCM).

4. The composition according to claim 1, wherein said intracellular components comprise nucleic acids.

5. The composition according to claim 1 wherein said fractionated extract comprises secreted peptides, secreted proteins and secondary metabolites.

6. The composition according to claim 1 wherein said fractionated extract comprises membrane proteins, periplasmic proteins, proteins arising from the flagellum, secreted peptides, secreted proteins and secondary metabolites.

7. The composition according to claim 1, wherein said fractionated extract comprises a protein profile, obtained by SDS-PAGE, which includes three principal bands corresponding to molecular weights ranging between 30 kDa and 36 kDa, 41 kDa and 45 kDa, and 47 kDa and 51 kDa, respectively.

8. The composition according to claim 1 further comprising and one or more typical dermatologically-compatible excipients.

9. The composition according to claim 1 wherein said fractionated extract comprises membrane proteins, periplasmic proteins, and proteins arising from the flagellum.

10. The composition according to claim 9, wherein said membrane proteins are selected from porins, OmpA, lipopolysaccharides and lipoproteins.

* * * * *